US011219555B2

(12) United States Patent
Schneider et al.

(10) Patent No.: US 11,219,555 B2
(45) Date of Patent: Jan. 11, 2022

(54) APPARATUSES AND METHODS FOR MAKING ABSORBENT ARTICLES WITH ELASTOMERIC LAMINATES

(71) Applicant: The Procter & Gamble Company, Cincinnati, OH (US)

(72) Inventors: Uwe Schneider, Cincinnati, OH (US); Kazuaki Tameishi, Kobe (JP)

(73) Assignee: The Procter & Gamble Company, Cincinnati, OH (US)

( * ) Notice: Subject to any disclaimer, the term of this patent is extended or adjusted under 35 U.S.C. 154(b) by 114 days.

(21) Appl. No.: 15/838,405

(22) Filed: Dec. 12, 2017

(65) Prior Publication Data
US 2018/0169964 A1 Jun. 21, 2018

Related U.S. Application Data

(60) Provisional application No. 62/581,278, filed on Nov. 3, 2017, provisional application No. 62/436,589, filed
(Continued)

(51) Int. Cl.
A61F 13/15 (2006.01)
A61F 13/49 (2006.01)
(Continued)

(52) U.S. Cl.
CPC .... A61F 13/15593 (2013.01); A61F 13/4902 (2013.01); A61F 13/49061 (2013.01);
(Continued)

(58) Field of Classification Search
CPC .......... A61F 13/15593; A61F 13/15601; A61F 13/15699; A61F 13/49011;
(Continued)

(56) References Cited

U.S. PATENT DOCUMENTS 3,113,225 A 12/1963 Kleesattel et al.
3,434,189 A 3/1969 Buck et al.
(Continued)

FOREIGN PATENT DOCUMENTS

CA 2158790 3/1996
CN 1276196 A 6/1999
(Continued)

OTHER PUBLICATIONS

Machine translation of JP 2008104853 date unknown.*
(Continued)

Primary Examiner — John L Goff, II
(74) Attorney, Agent, or Firm — Charles R. Matson

(57) ABSTRACT

The present disclosure relates to methods and apparatuses for making elastomeric laminates with deactivated regions that may be used as components of absorbent articles. The methods and apparatuses may be configured with a pattern roll and a pressing surface adjacent the pattern roll. The pattern roll may include a bonding surface and a protuberance. As the pattern roll rotates, first and second substrates are welded together between the bonding surface and the pressing surface to create bonds between the first and second substrates. As the pattern roll continues to rotate, the first and second substrates and one or more stretched elastic strands are compressed between the pressing surface and the protuberance to sever the one or more stretched elastic strands to create deactivated regions in the elastomeric laminate. The processes and apparatuses may be configured to help prevent ends of the severed elastic strands from retracting in an uncontrolled fashion.

20 Claims, 25 Drawing Sheets

Related U.S. Application Data on Dec. 20, 2016, provisional application No. 62/483,965, filed on Apr. 11, 2017, provisional application No. 62/553,149, filed on Sep. 1, 2017, provisional application No. 62/553,171, filed on Sep. 1, 2017, provisional application No. 62/553,538, filed on Sep. 1, 2017.

(51) Int. Cl.

| | |
|---|---|
| B32B 27/12 | (2006.01) |
| D01F 6/04 | (2006.01) |
| A61F 13/53 | (2006.01) |
| D01D 5/08 | (2006.01) |
| B29C 65/08 | (2006.01) |
| B29C 65/48 | (2006.01) |
| B29L 31/48 | (2006.01) |
| B05C 1/08 | (2006.01) |
| B32B 37/14 | (2006.01) |
| B65H 39/16 | (2006.01) |
| B65H 51/30 | (2006.01) |
| B29C 65/00 | (2006.01) |
| B29C 65/74 | (2006.01) |
| B29K 701/12 | (2006.01) |
| A61F 13/64 | (2006.01) |
| A61F 13/84 | (2006.01) |
| B32B 5/04 | (2006.01) |
| B32B 37/00 | (2006.01) |
| B32B 37/12 | (2006.01) |
| D04H 3/12 | (2006.01) |
| A61F 13/56 | (2006.01) |
| B32B 37/22 | (2006.01) |
| A61F 13/513 | (2006.01) |

(52) U.S. Cl.
CPC ... *A61F 13/15601* (2013.01); *A61F 13/15699* (2013.01); *A61F 13/15739* (2013.01); *A61F 13/15764* (2013.01); *A61F 13/49012* (2013.01); *A61F 13/49015* (2013.01); *A61F 13/49017* (2013.01); *A61F 13/49019* (2013.01); *A61F 13/53* (2013.01); *A61F 13/5622* (2013.01); *A61F 13/64* (2013.01); *A61F 2013/1552* (2013.01); *A61F 2013/1591* (2013.01); *A61F 2013/15292* (2013.01); *A61F 2013/15373* (2013.01); *A61F 2013/15406* (2013.01); *A61F 2013/15447* (2013.01); *A61F 2013/15552* (2013.01); *A61F 2013/15869* (2013.01); *A61F 2013/15918* (2013.01); *A61F 2013/15959* (2013.01); *A61F 2013/49022* (2013.01); *A61F 2013/49025* (2013.01); *A61F 2013/49026* (2013.01); *A61F 2013/49074* (2013.01); *A61F 2013/49092* (2013.01); *A61F 2013/49093* (2013.01); *A61F 2013/51322* (2013.01); *A61F 2013/53043* (2013.01); *A61F 2013/530343* (2013.01); *A61F 2013/8497* (2013.01); *B05C 1/0808* (2013.01); *B29C 65/08* (2013.01); *B29C 65/086* (2013.01); *B29C 65/48* (2013.01); *B29C 65/74* (2013.01); *B29C 66/01* (2013.01); *B29C 66/344* (2013.01); *B29C 66/8141* (2013.01); *B29C 66/83411* (2013.01); *B29K 2701/12* (2013.01); *B29K 2995/0046* (2013.01); *B29L 2031/4878* (2013.01); *B32B 5/04* (2013.01); *B32B 27/12* (2013.01); *B32B 37/0053* (2013.01); *B32B 37/12* (2013.01); *B32B 37/144* (2013.01); *B32B 37/22* (2013.01); *B32B 2305/20* (2013.01); *B32B 2307/51* (2013.01); *B32B 2307/726* (2013.01); *B32B 2555/02* (2013.01); *B65H 39/16* (2013.01); *B65H 51/30* (2013.01); *C08J 2300/26* (2013.01); *D01D 5/08* (2013.01); *D01F 6/04* (2013.01); *D04H 3/12* (2013.01)

(58) Field of Classification Search
CPC .......... A61F 13/49012; A61F 13/49014; A61F 13/49015; A61F 13/49017; A61F 13/49019; A61F 13/49061; A61F 13/51464; A61F 13/4902; A61F 13/496; A61F 13/15739; A61F 13/15869; A61F 2013/15869; A61F 2013/15878; A61F 2013/15886; A61F 2013/15861; A61F 2013/49025; A61F 2013/49031; A61F 2013/49036; B29C 65/08; B29C 65/083; B29C 65/087; B29C 65/085; B29C 65/086; B29C 65/088; B29C 65/74; B29C 65/743; B29C 65/7435; B29C 65/7443; B29C 65/7455; B29C 66/344; B29C 66/8141; B29C 66/83411; B29C 66/81435; B32B 37/0053; B32B 37/0076; B32B 37/0084; B32B 37/30; B32B 37/144; B32B 38/0004; B32B 38/1825; B32B 38/1875; B32B 2038/0028; B32B 2307/51; B32B 2555/02

See application file for complete search history.

(56) References Cited

U.S. PATENT DOCUMENTS

| | | |
|---|---|---|
| 3,508,722 A | 4/1970 | Kohl |
| 3,562,041 A | 2/1971 | Robertson |
| 3,575,782 A | 4/1971 | Hansen |
| 3,733,238 A | 5/1973 | Long et al. |
| 3,860,003 A | 1/1975 | Buell |
| 3,871,378 A | 3/1975 | Duncan et al. |
| 4,251,587 A | 2/1981 | Mimura et al. |
| 4,333,979 A | 6/1982 | Sciaraffa et al. |
| 4,525,905 A | 7/1985 | Bogucki-Land |
| 4,610,678 A | 9/1986 | Weisman et al. |
| 4,640,859 A | 2/1987 | Hansen et al. |
| 4,657,539 A | 4/1987 | Hasse |
| 4,673,402 A | 6/1987 | Weisman et al. |
| 4,695,278 A | 9/1987 | Lawson |
| 4,704,115 A | 11/1987 | Buell |
| 4,741,941 A | 5/1988 | Englebert et al. |
| 4,776,911 A | 10/1988 | Uda et al. |
| 4,795,454 A | 1/1989 | Dragoo |
| 4,834,735 A | 5/1989 | Alemany et al. |
| 4,854,984 A | 8/1989 | Ball et al. |
| 4,888,231 A | 12/1989 | Angstadt |
| 4,909,803 A | 3/1990 | Aziz et al. |
| 4,940,464 A | 7/1990 | Van Gompel et al. |
| 4,984,584 A | 1/1991 | Hansen et al. |
| 5,003,676 A | 4/1991 | McFalls |
| 5,060,881 A | 10/1991 | Bogucki-Land |
| 5,092,861 A | 3/1992 | Nomura et al. |
| 5,110,403 A | 5/1992 | Ehlert |
| 5,167,897 A | 12/1992 | Weber et al. |
| 5,246,433 A | 9/1993 | Hasse et al. |
| 5,334,289 A | 8/1994 | Trokhan et al. |
| 5,342,341 A | 8/1994 | Igaue et al. |
| 5,360,420 A | 11/1994 | Cook et al. |
| 5,393,360 A | 2/1995 | Bridges et al. |
| 5,413,849 A | 5/1995 | Austin et al. |
| 5,514,523 A | 5/1996 | Trokhan et al. |
| 5,531,729 A | 7/1996 | Coles et al. |
| 5,558,658 A | 9/1996 | Menard et al. |
| 5,562,646 A | 10/1996 | Goldman et al. |
| 5,569,234 A | 10/1996 | Buell et al. |
| 5,575,874 A | 11/1996 | Griesbach, III et al. |
| 5,599,335 A | 2/1997 | Goldman et al. |

(56) References Cited

U.S. PATENT DOCUMENTS

| | | |
|---|---|---|
| 5,599,420 A | 2/1997 | Yeo et al. |
| 5,628,097 A | 5/1997 | Benson et al. |
| 5,643,588 A | 7/1997 | Roe et al. |
| 5,643,653 A | 7/1997 | Griesbach, III et al. |
| 5,669,894 A | 9/1997 | Goldman et al. |
| 5,674,216 A | 10/1997 | Buell et al. |
| 5,702,551 A | 12/1997 | Huber et al. |
| 5,775,380 A | 7/1998 | Roelstraete et al. |
| 5,827,259 A | 10/1998 | Laux et al. |
| 5,858,504 A | 1/1999 | Steven |
| 5,887,322 A | 3/1999 | Hartzheim et al. |
| 5,895,623 A | 4/1999 | Trokhan et al. |
| 5,897,545 A | 4/1999 | Kline et al. |
| 5,916,661 A | 6/1999 | Benson et al. |
| 5,957,908 A | 9/1999 | Kline et al. |
| 5,968,025 A | 10/1999 | Roe et al. |
| 5,993,433 A | 11/1999 | St. Louis et al. |
| 5,997,521 A | 12/1999 | Robles et al. |
| 6,036,796 A | 3/2000 | Halbert et al. |
| 6,043,168 A | 3/2000 | Colman et al. |
| 6,107,537 A | 8/2000 | Elder et al. |
| 6,107,539 A | 8/2000 | Palumbo et al. |
| 6,118,041 A | 9/2000 | Roe et al. |
| 6,120,487 A | 9/2000 | Ashton |
| 6,120,489 A | 9/2000 | Johnson et al. |
| 6,139,941 A | 10/2000 | Jankevics et al. |
| 6,153,209 A | 11/2000 | Vega et al. |
| 6,248,195 B1 | 6/2001 | Schmitz |
| 6,248,197 B1 | 6/2001 | Nakanishi et al. |
| 6,291,039 B1 | 9/2001 | Combe et al. |
| 6,319,239 B1 | 11/2001 | Daniels et al. |
| 6,361,638 B2 | 3/2002 | Takai et al. |
| 6,383,431 B1 | 5/2002 | Dobrin et al. |
| 6,395,957 B1 | 5/2002 | Chen et al. |
| 6,410,129 B2 | 6/2002 | Zhang et al. |
| 6,426,444 B2 | 7/2002 | Roe et al. |
| 6,475,600 B1 | 11/2002 | Morman et al. |
| 6,478,785 B1 | 11/2002 | Ashton et al. |
| 6,482,191 B1 | 11/2002 | Roe et al. |
| 6,508,641 B1 | 1/2003 | Kubik |
| 6,545,197 B1 | 4/2003 | Muller et al. |
| 6,554,815 B1 | 4/2003 | Umebayashi |
| 6,586,652 B1 | 7/2003 | Roe et al. |
| 6,617,016 B2 | 9/2003 | Zhang et al. |
| 6,627,787 B1 | 9/2003 | Roe et al. |
| 6,632,504 B1 | 10/2003 | Gillespie et al. |
| 6,645,330 B2 | 11/2003 | Pargass et al. |
| 6,673,418 B1 | 1/2004 | DeOlivera et al. |
| 6,676,054 B2 | 1/2004 | Heaney et al. |
| 6,702,798 B2 | 3/2004 | Christoffel et al. |
| 6,790,798 B1 | 9/2004 | Suzuki et al. |
| 6,821,301 B2 | 11/2004 | Azuse et al. |
| 6,825,393 B2 | 11/2004 | Roe et al. |
| 6,861,571 B1 | 3/2005 | Roe et al. |
| 7,008,685 B2 | 3/2006 | Groitzsch et al. |
| 7,118,558 B2 | 10/2006 | Wu et al. |
| 7,465,367 B2 | 12/2008 | Day |
| 7,569,039 B2 | 8/2009 | Matsuda et al. |
| 7,582,348 B2 | 9/2009 | Ando et al. |
| 7,642,398 B2 | 1/2010 | Järpenberg et al. |
| 7,708,849 B2 | 5/2010 | McCabe |
| 7,777,094 B2 | 8/2010 | Mori et al. |
| 7,861,756 B2 | 1/2011 | Jenquin et al. |
| 7,878,447 B2 | 2/2011 | Hartzheim |
| 7,901,393 B2 | 3/2011 | Matsuda et al. |
| 7,905,446 B2 | 3/2011 | Hartzheim |
| 7,954,213 B2 | 6/2011 | Mizutani et al. |
| 8,093,161 B2 | 1/2012 | Bansal et al. |
| 8,143,177 B2 | 3/2012 | Noda et al. |
| 8,186,296 B2 | 5/2012 | Brown et al. |
| 8,226,625 B2 | 7/2012 | Turner et al. |
| 8,308,706 B2 | 11/2012 | Fukae |
| 8,377,554 B2 | 2/2013 | Martin et al. |
| 8,388,594 B2 | 3/2013 | Turner et al. |
| 8,440,043 B1 | 5/2013 | Schneider et al. |
| 8,585,666 B2 | 11/2013 | Weisman et al. |
| 8,647,319 B2 | 2/2014 | Een et al. |
| 8,729,332 B2 | 5/2014 | Takahashi et al. |
| 8,778,127 B2 | 7/2014 | Schneider et al. |
| 8,853,108 B2 | 10/2014 | Ahoniemi et al. |
| 8,906,275 B2 | 12/2014 | Davis et al. |
| 8,939,957 B2 | 1/2015 | Raycheck et al. |
| 9,005,392 B2 | 4/2015 | Schneider et al. |
| 9,039,855 B2 | 5/2015 | Schneider et al. |
| 9,050,213 B2 | 6/2015 | LaVon et al. |
| 9,156,648 B2 | 10/2015 | Yamamoto |
| 9,168,182 B2 | 10/2015 | Hargett et al. |
| 9,198,804 B2 | 12/2015 | Nakamura et al. |
| 9,226,861 B2 | 1/2016 | LaVon et al. |
| 9,248,054 B2 | 2/2016 | Brown et al. |
| 9,265,672 B2 | 2/2016 | Brown et al. |
| 9,295,590 B2 | 3/2016 | Brown et al. |
| 9,370,775 B2 | 6/2016 | Harvey et al. |
| 9,440,043 B2 | 9/2016 | Schneider et al. |
| 9,453,303 B2 | 9/2016 | Aberg et al. |
| 9,539,735 B2 | 1/2017 | Ferguson et al. |
| 9,732,454 B2 | 8/2017 | Davis et al. |
| 9,758,339 B2 | 9/2017 | Yanez, Jr. et al. |
| 9,795,520 B2 | 10/2017 | Kaneko et al. |
| 9,877,876 B2 | 1/2018 | Huang et al. |
| 10,190,244 B2 | 1/2019 | Ashraf et al. |
| 10,596,045 B2 | 3/2020 | Koshijima et al. |
| 10,792,194 B2 | 10/2020 | Hohm et al. |
| 2001/0030014 A1 | 10/2001 | Kwok |
| 2002/0026660 A1 | 3/2002 | Goda |
| 2002/0046802 A1 | 4/2002 | Tachibana et al. |
| 2002/0072723 A1 | 6/2002 | Ronn et al. |
| 2002/0099347 A1 | 7/2002 | Chen et al. |
| 2002/0103469 A1 | 8/2002 | Chen et al. |
| 2002/0134067 A1 | 9/2002 | Heaney et al. |
| 2002/0153271 A1 | 10/2002 | McManus et al. |
| 2002/0177829 A1 | 11/2002 | Fell et al. |
| 2003/0044585 A1 | 3/2003 | Taylor et al. |
| 2003/0070780 A1 | 4/2003 | Chen et al. |
| 2003/0087056 A1 | 5/2003 | Ducker et al. |
| 2003/0093045 A1 | 5/2003 | Jensen |
| 2003/0119404 A1 | 6/2003 | Belau et al. |
| 2003/0125687 A1 | 7/2003 | Gubernick et al. |
| 2003/0144643 A1 | 7/2003 | Järpenberg et al. |
| 2003/0203162 A1 | 10/2003 | Christopher et al. |
| 2003/0233082 A1 | 12/2003 | Kline et al. |
| 2004/0006323 A1 | 1/2004 | Hall et al. |
| 2004/0030317 A1 | 2/2004 | Torigoshi |
| 2004/0059309 A1 | 3/2004 | Nortman |
| 2004/0097895 A1 | 5/2004 | Busam et al. |
| 2004/0127881 A1 | 7/2004 | Stevens et al. |
| 2004/0133180 A1 | 7/2004 | Mori et al. |
| 2004/0158212 A1 | 8/2004 | Ponomarenko et al. |
| 2004/0158217 A1 | 8/2004 | Wu et al. |
| 2004/0219854 A1 | 11/2004 | Groitzsch et al. |
| 2004/0230171 A1 | 11/2004 | Ando et al. |
| 2005/0013975 A1 | 1/2005 | Brock et al. |
| 2005/0107764 A1 | 5/2005 | Matsuda et al. |
| 2005/0148971 A1 | 7/2005 | Kuroda et al. |
| 2005/0230037 A1 | 10/2005 | Jenquin et al. |
| 2005/0244640 A1 | 11/2005 | Riswick et al. |
| 2005/0267431 A1 | 12/2005 | Sasaki et al. |
| 2006/0047260 A1 | 3/2006 | Ashton et al. |
| 2006/0069373 A1 | 3/2006 | Schlinz et al. |
| 2006/0087053 A1 | 4/2006 | O'Donnell et al. |
| 2006/0105075 A1 | 5/2006 | Otsubo |
| 2006/0189954 A1 | 8/2006 | Kudo et al. |
| 2006/0228969 A1 | 10/2006 | Erdman |
| 2006/0270302 A1 | 11/2006 | Ando et al. |
| 2007/0026753 A1 | 2/2007 | Neely et al. |
| 2007/0045143 A1 | 3/2007 | Clough et al. |
| 2007/0045144 A1 | 3/2007 | Wheeler et al. |
| 2007/0131335 A1 | 6/2007 | Zhou et al. |
| 2007/0141311 A1 | 6/2007 | Mleziva et al. |
| 2007/0179466 A1 | 8/2007 | Tremblay et al. |
| 2007/0196650 A1 | 8/2007 | Yamamoto et al. |
| 2008/0134487 A1 | 6/2008 | Hartono |
| 2008/0149292 A1 | 6/2008 | Scherb |
| 2008/0161768 A1 | 7/2008 | Baba et al. |

(56) References Cited

U.S. PATENT DOCUMENTS

| | | |
|---|---|---|
| 2008/0287897 A1 | 11/2008 | Guzman et al. |
| 2009/0177176 A1 | 7/2009 | Saito |
| 2009/0204093 A1 | 8/2009 | Vasic et al. |
| 2009/0312730 A1 | 12/2009 | LaVon et al. |
| 2010/0022151 A1 | 1/2010 | Malowaniec |
| 2010/0036346 A1 | 2/2010 | Hammons |
| 2010/0048072 A1 | 2/2010 | Kauschke |
| 2010/0075103 A1 | 3/2010 | Miyamoto |
| 2010/0076394 A1* | 3/2010 | Hayase ............ A61F 13/15593 604/385.29 |
| 2010/0248575 A1 | 9/2010 | Malz |
| 2010/0307668 A1 | 12/2010 | Lange et al. |
| 2011/0092943 A1 | 4/2011 | Bishop et al. |
| 2011/0118689 A1* | 5/2011 | Een ................ A61F 13/49011 604/385.3 |
| 2011/0120897 A1 | 5/2011 | Takahashi |
| 2011/0250378 A1 | 10/2011 | Eaton et al. |
| 2012/0004633 A1 | 1/2012 | Marcelo et al. |
| 2012/0061015 A1 | 3/2012 | LaVon et al. |
| 2012/0061016 A1 | 3/2012 | LaVon et al. |
| 2012/0071852 A1 | 3/2012 | Tsang et al. |
| 2012/0095429 A1* | 4/2012 | Kobayashi ........ A61F 13/15804 604/385.16 |
| 2012/0271267 A1 | 10/2012 | Love et al. |
| 2012/0277713 A1 | 11/2012 | Raycheck et al. |
| 2012/0323206 A1 | 12/2012 | McMorrow et al. |
| 2013/0032656 A1 | 2/2013 | Yamamoto et al. |
| 2013/0072887 A1 | 3/2013 | LaVon et al. |
| 2013/0102982 A1 | 4/2013 | Nakano et al. |
| 2013/0001125 A1 | 5/2013 | Gaspari et al. |
| 2013/0139960 A1 | 6/2013 | Maruyama et al. |
| 2013/0171421 A1 | 7/2013 | Weisman et al. |
| 2013/0002113 A1 | 8/2013 | LaVon et al. |
| 2013/0199696 A1 | 8/2013 | Schneider et al. |
| 2013/0199707 A1 | 8/2013 | Schneider |
| 2013/0211356 A1 | 8/2013 | Nishikawa et al. |
| 2013/0002615 A1 | 10/2013 | Fujkawa et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0306226 A1 | 11/2013 | Zink et al. |
| 2014/0000794 A1 | 1/2014 | Hamilton et al. |
| 2014/0005621 A1 | 1/2014 | Roe et al. |
| 2014/0018759 A1 | 1/2014 | Jayasinghe et al. |
| 2014/0041797 A1 | 2/2014 | Schneider |
| 2014/0107605 A1 | 4/2014 | Schroer, Jr. et al. |
| 2014/0127460 A1 | 5/2014 | Xu et al. |
| 2014/0136893 A1 | 5/2014 | Xie et al. |
| 2014/0148773 A1 | 5/2014 | Brown et al. |
| 2014/0234575 A1 | 8/2014 | Mitsuno et al. |
| 2014/0235127 A1 | 8/2014 | DeJesus et al. |
| 2014/0257231 A1 | 9/2014 | Wang et al. |
| 2014/0276517 A1 | 9/2014 | Chester et al. |
| 2014/0288521 A1 | 9/2014 | Wade et al. |
| 2014/0296815 A1 | 10/2014 | Takken et al. |
| 2014/0302286 A1 | 10/2014 | Okuda et al. |
| 2014/0305570 A1 | 10/2014 | Matsunaga et al. |
| 2014/0324009 A1 | 10/2014 | Lee et al. |
| 2014/0343525 A1 | 11/2014 | Roh et al. |
| 2014/0377506 A1 | 12/2014 | Eckstein et al. |
| 2014/0377513 A1 | 12/2014 | Galie et al. |
| 2015/0083309 A1 | 3/2015 | Long et al. |
| 2015/0126956 A1 | 5/2015 | Raycheck et al. |
| 2015/0136893 A1 | 5/2015 | Koskol |
| 2015/0164708 A1 | 6/2015 | Hashimoto et al. |
| 2015/0167207 A1 | 6/2015 | Bongartz et al. |
| 2015/0173967 A1 | 6/2015 | Kreuzer et al. |
| 2015/0230995 A1 | 8/2015 | Kaneko et al. |
| 2015/0245958 A1 | 9/2015 | Chmielewski et al. |
| 2015/0257941 A1 | 9/2015 | Eckstein et al. |
| 2015/0282999 A1 | 10/2015 | Arizti et al. |
| 2015/0320612 A1 | 11/2015 | Seitz et al. |
| 2015/0320613 A1 | 11/2015 | Seitz et al. |
| 2015/0320619 A1 | 11/2015 | Seitz et al. |
| 2015/0320620 A1 | 11/2015 | Seitz et al. |
| 2015/0320622 A1 | 11/2015 | Seitz et al. |
| 2015/0328056 A1 | 11/2015 | Een et al. |
| 2015/0351972 A1 | 12/2015 | Bing-Wo |
| 2016/0058624 A1 | 3/2016 | Hohm et al. |
| 2016/0058627 A1 | 3/2016 | Barnes et al. |
| 2016/0067119 A1 | 3/2016 | Weisman et al. |
| 2016/0100989 A1 | 4/2016 | Seitz et al. |
| 2016/0100997 A1 | 4/2016 | Seitz et al. |
| 2016/0106633 A1 | 4/2016 | Nagata et al. |
| 2016/0129661 A1 | 5/2016 | Arora et al. |
| 2016/0136009 A1 | 5/2016 | Weisman et al. |
| 2016/0228305 A1 | 8/2016 | Gualtieri et al. |
| 2016/0270977 A1 | 9/2016 | Surushi et al. |
| 2016/0331600 A1 | 11/2016 | Polidori et al. |
| 2017/0014281 A1 | 1/2017 | Xie et al. |
| 2017/0027774 A1 | 2/2017 | Ashraf et al. |
| 2017/0029993 A1 | 2/2017 | Ashraf et al. |
| 2017/0029994 A1 | 2/2017 | Ashraf et al. |
| 2017/0056256 A1 | 3/2017 | Smith et al. |
| 2017/0065461 A1 | 3/2017 | Schneider |
| 2017/0079852 A1 | 3/2017 | Fujima et al. |
| 2017/0119595 A1 | 5/2017 | Carla et al. |
| 2017/0191198 A1 | 7/2017 | Ashraf et al. |
| 2017/0258650 A1 | 9/2017 | Rosati et al. |
| 2017/0281417 A1* | 10/2017 | Ishikawa ................ A61F 13/49 |
| 2017/0319403 A1 | 11/2017 | Bewick-Sonntag et al. |
| 2017/0348163 A1 | 12/2017 | Lakso et al. |
| 2018/0092784 A1 | 4/2018 | Wade et al. |
| 2018/0140473 A1* | 5/2018 | Koshijima ......... B29D 99/0064 |
| 2018/0168874 A1 | 6/2018 | LaVon et al. |
| 2018/0168875 A1 | 6/2018 | LaVon et al. |
| 2018/0168876 A1 | 6/2018 | LaVon et al. |
| 2018/0168877 A1 | 6/2018 | Schneider et al. |
| 2018/0168878 A1 | 6/2018 | Schneider et al. |
| 2018/0168879 A1 | 6/2018 | Schneider et al. |
| 2018/0168880 A1 | 6/2018 | Schneider et al. |
| 2018/0168885 A1 | 6/2018 | Zink, II et al. |
| 2018/0168887 A1 | 6/2018 | LaVon et al. |
| 2018/0168888 A1 | 6/2018 | Zink, II et al. |
| 2018/0168889 A1 | 6/2018 | LaVon et al. |
| 2018/0168890 A1 | 6/2018 | LaVon et al. |
| 2018/0168891 A1 | 6/2018 | Wise et al. |
| 2018/0168892 A1 | 6/2018 | LaVon et al. |
| 2018/0168893 A1 | 6/2018 | Ashraf et al. |
| 2018/0169964 A1 | 6/2018 | Schneider et al. |
| 2018/0170026 A1 | 6/2018 | Schneider et al. |
| 2018/0170027 A1 | 6/2018 | Schneider et al. |
| 2018/0214318 A1 | 8/2018 | Ashraf et al. |
| 2018/0214321 A1 | 8/2018 | Ashraf et al. |
| 2018/0216269 A1 | 8/2018 | Ashraf et al. |
| 2018/0216270 A1 | 8/2018 | Ashraf et al. |
| 2018/0216271 A1 | 8/2018 | Ashraf et al. |
| 2018/0333311 A1 | 11/2018 | Maki et al. |
| 2019/0003079 A1 | 1/2019 | Ashraf et al. |
| 2019/0003080 A1 | 1/2019 | Ashraf et al. |
| 2019/0070041 A1 | 3/2019 | Schneider et al. |
| 2019/0070042 A1 | 3/2019 | LaVon et al. |
| 2019/0112737 A1 | 4/2019 | Ashraf et al. |
| 2019/0254881 A1 | 8/2019 | Ishikawa et al. |
| 2019/0298586 A1 | 10/2019 | Ashraf et al. |
| 2019/0298587 A1 | 10/2019 | Ashraf et al. |
| 2019/0246196 A1 | 12/2019 | Han et al. |
| 2019/0374392 A1 | 12/2019 | Ninomiya et al. |
| 2019/0374404 A1 | 12/2019 | Ninomiya et al. |
| 2020/0155370 A1 | 5/2020 | Ohtsubo et al. |
| 2020/0155371 A1 | 5/2020 | Ohtsubo et al. |
| 2020/0206040 A1 | 7/2020 | Andrews et al. |
| 2020/0214901 A1 | 7/2020 | Andrews et al. |
| 2020/0298545 A1 | 9/2020 | Andrews et al. |

FOREIGN PATENT DOCUMENTS

| | | |
|---|---|---|
| CN | 1685099 | 10/2005 |
| CN | 101746057 A | 6/2010 |
| CN | 105997351 A | 10/2016 |
| EP | 0989218 A1 | 3/2000 |
| EP | 1305248 B1 | 5/2003 |

(56) References Cited

FOREIGN PATENT DOCUMENTS

| | | |
|---|---|---|
| EP | 1452157 A1 | 9/2004 |
| EP | 1473148 A1 | 11/2004 |
| EP | 1393701 B1 | 7/2013 |
| EP | 3056176 A1 | 8/2016 |
| EP | 3 092 997 B1 | 8/2017 |
| EP | 3251642 A1 | 12/2017 |
| EP | 3257488 A1 | 12/2017 |
| EP | 3563817 A1 | 11/2019 |
| JP | H03213543 A | 9/1991 |
| JP | H0430847 A | 2/1992 |
| JP | H 06254117 | 9/1994 |
| JP | H08071107 A | 3/1996 |
| JP | H08132576 A | 5/1996 |
| JP | 2000026015 A | 1/2000 |
| JP | 2000160460 | 6/2000 |
| JP | 3086141 B2 | 9/2000 |
| JP | 2002035029 A | 2/2002 |
| JP | 2002178428 A | 6/2002 |
| JP | 2002248127 A | 9/2002 |
| JP | 2003521949 | 7/2003 |
| JP | 2004081365 | 3/2004 |
| JP | 2004229857 A | 8/2004 |
| JP | 2004237410 A | 8/2004 |
| JP | 2004254862 A | 9/2004 |
| JP | 2004298362 A | 10/2004 |
| JP | 2005320636 A | 11/2005 |
| JP | 2006149747 A | 6/2006 |
| JP | 2006149749 A | 6/2006 |
| JP | 2006204673 A | 12/2006 |
| JP | 2007190397 A | 8/2007 |
| JP | 2008029749 A | 2/2008 |
| JP | 2008055198 A | 3/2008 |
| JP | 2008104853 A * | 5/2008 ......... B29C 66/1122 |
| JP | 2008105425 A | 5/2008 |
| JP | 2008154998 | 5/2008 |
| JP | 2008148942 A | 7/2008 |
| JP | 2008179128 A | 8/2008 |
| JP | 2008194493 A | 8/2008 |
| JP | 2008229006 A | 10/2008 |
| JP | 2008229007 A | 10/2008 |
| JP | 2008253290 | 10/2008 |
| JP | 2008260131 A | 10/2008 |
| JP | 2014188042 | 10/2008 |
| JP | 2008264480 A | 11/2008 |
| JP | 2008272250 A | 11/2008 |
| JP | 2008272253 A | 11/2008 |
| JP | 2008296585 A | 12/2008 |
| JP | 2009000161 A | 1/2009 |
| JP | 2009039341 A | 2/2009 |
| JP | 2009056156 A | 3/2009 |
| JP | 2009106667 | 5/2009 |
| JP | 2009172231 A | 8/2009 |
| JP | 2009240804 A | 10/2009 |
| JP | 2009241607 A | 10/2009 |
| JP | 2010131833 A | 6/2010 |
| JP | 2011015707 | 1/2011 |
| JP | 2011111165 | 6/2011 |
| JP | 2011178124 A | 9/2011 |
| JP | 2011225000 A | 11/2011 |
| JP | 2012050882 A | 3/2012 |
| JP | 2012050883 A | 3/2012 |
| JP | 2012115358 A | 6/2012 |
| JP | 2012521498 | 9/2012 |
| JP | 5124187 B2 | 11/2012 |
| JP | 5124188 B2 | 11/2012 |
| JP | 2013138795 A | 7/2013 |
| JP | 2014111222 | 6/2014 |
| JP | 2014097257 | 10/2014 |
| JP | 2015510831 | 4/2015 |
| JP | 2015521499 | 7/2015 |
| JP | 2016013687 A | 1/2016 |
| JP | 2016016536 A | 2/2016 |
| JP | 5942819 B2 | 6/2016 |
| JP | 2016193199 A | 11/2016 |
| JP | 6149635 B2 | 6/2017 |
| JP | 2020054741 A | 4/2018 |
| JP | 2020054742 A | 4/2018 |
| JP | 2020054744 A | 4/2018 |
| JP | 2020054745 A | 4/2018 |
| JP | 2019081304 | 5/2019 |
| JP | 2019166804 | 10/2019 |
| JP | 2019181807 | 10/2019 |
| WO | WO 2017105997 | 3/1996 |
| WO | WO 9925296 | 5/1999 |
| WO | WO 03/059603 | 7/2003 |
| WO | WO 2008123348 | 2/2013 |
| WO | WO 2003015681 | 6/2013 |
| WO | WO2014084168 A1 | 6/2014 |
| WO | WO 2013084977 | 11/2014 |
| WO | WO-2016047320 A1 * | 3/2016 ............. A61F 13/15 |
| WO | WO2016056092 A1 | 4/2016 |
| WO | WO2016056093 A1 | 4/2016 |
| WO | WO2016063346 A1 | 4/2016 |
| WO | WO2016067387 A1 | 5/2016 |
| WO | WO2016071981 A1 | 5/2016 |
| WO | WO2016075974 A1 | 5/2016 |
| WO | WO2016098416 A1 | 6/2016 |
| WO | WO2016104412 A1 | 6/2016 |
| WO | WO2016104422 A1 | 6/2016 |
| WO | WO2016158499 A1 | 10/2016 |
| WO | WO2016158746 A1 | 10/2016 |
| WO | WO2016208502 A1 | 12/2016 |
| WO | WO2016208513 A1 | 12/2016 |
| WO | WO 2014196669 | 6/2017 |
| WO | WO 2018061288 | 4/2018 |
| WO | WO 2018084145 | 5/2018 |
| WO | WO 2018154680 A1 | 8/2018 |
| WO | WO 2018154682 A1 | 8/2018 |
| WO | WO 2018167836 A1 | 8/2018 |
| WO | WO 2019046363 | 3/2019 |
| WO | WO 2019111203 | 6/2019 |
| WO | WO 2019150802 A1 | 8/2019 |

OTHER PUBLICATIONS

PCT International Search Report, dated Mar. 19, 2018, 12 pages.
All Office Actions, U.S. Appl. No. 15/831,448.
All Office Actions, U.S. Appl. No. 15/831,464.
All Office Actions, U.S. Appl. No. 15/832,929.
All Office Actions, U.S. Appl. No. 15/833,057.
All Office Actions, U.S. Appl. No. 15/839,896.
All Office Actions, U.S. Appl. No. 15/846,382.
All Office Actions, U.S. Appl. No. 16/115,617.
3D Nonwovens Developments for textured nonwovens; Detlef Frey; http://web.archive.org/web/20170919080326/https://www.reicofil.com/en/pages/3d_nonwovens, Sep. 19, 2017.
PCT International Search Report, PCT/US2017/065755, dated Mar. 19, 2018.
American Cancer Society—What Cancer Patients Their Families and Caregivers Need to Know About COVID 19—Is Impacting Our Patient Services.
ASTM—Standard Tables of Body Measurements for Adult Females Misses Figure Type Size Range 00-20.
ASTM—Standard Tables of Body Measurements for Children Infant Size—Preemie to 24 Months.

* cited by examiner

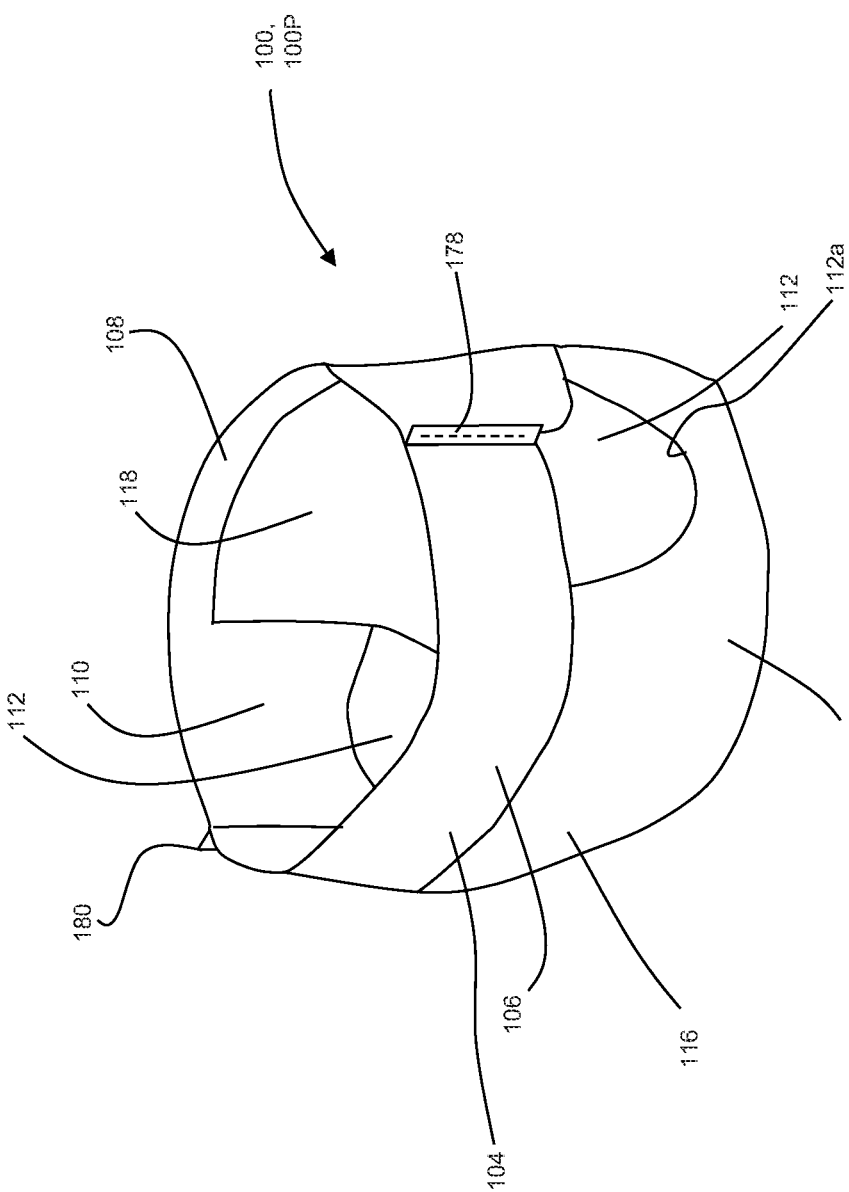

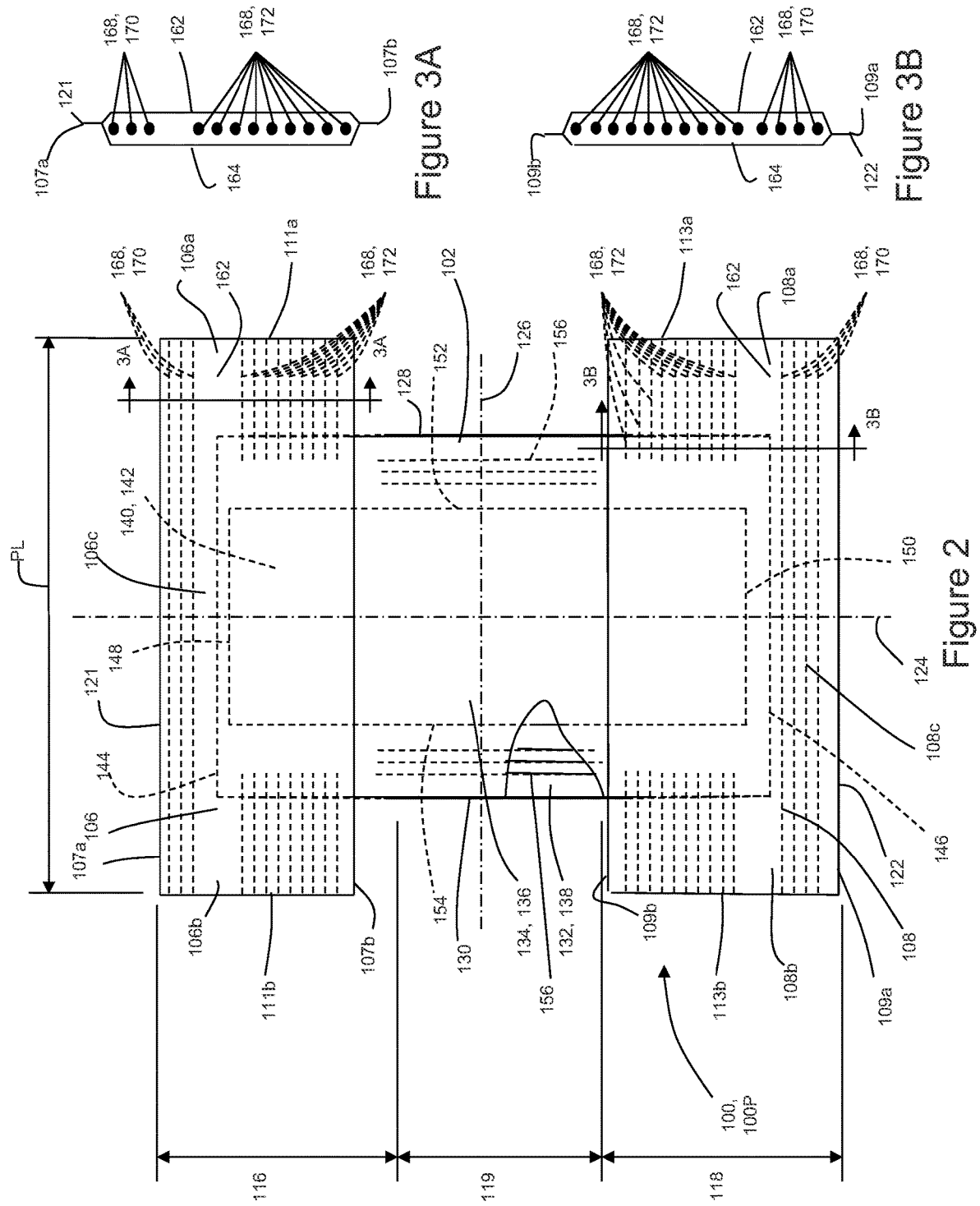

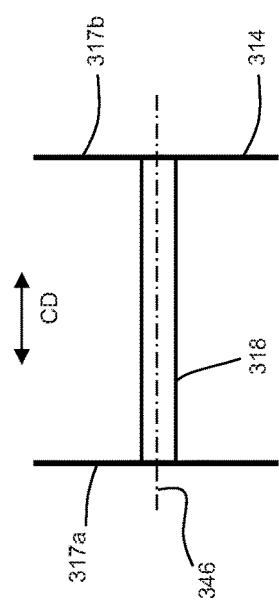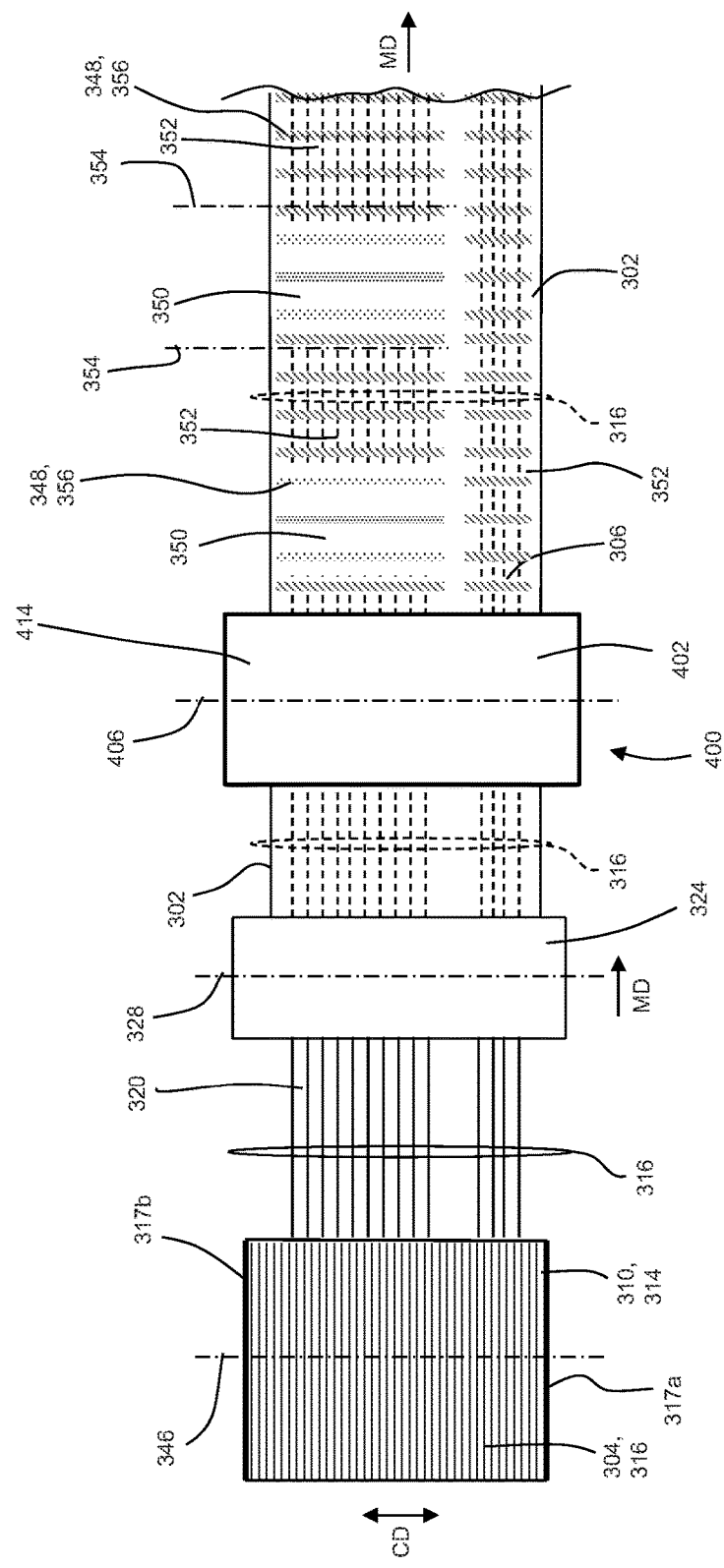

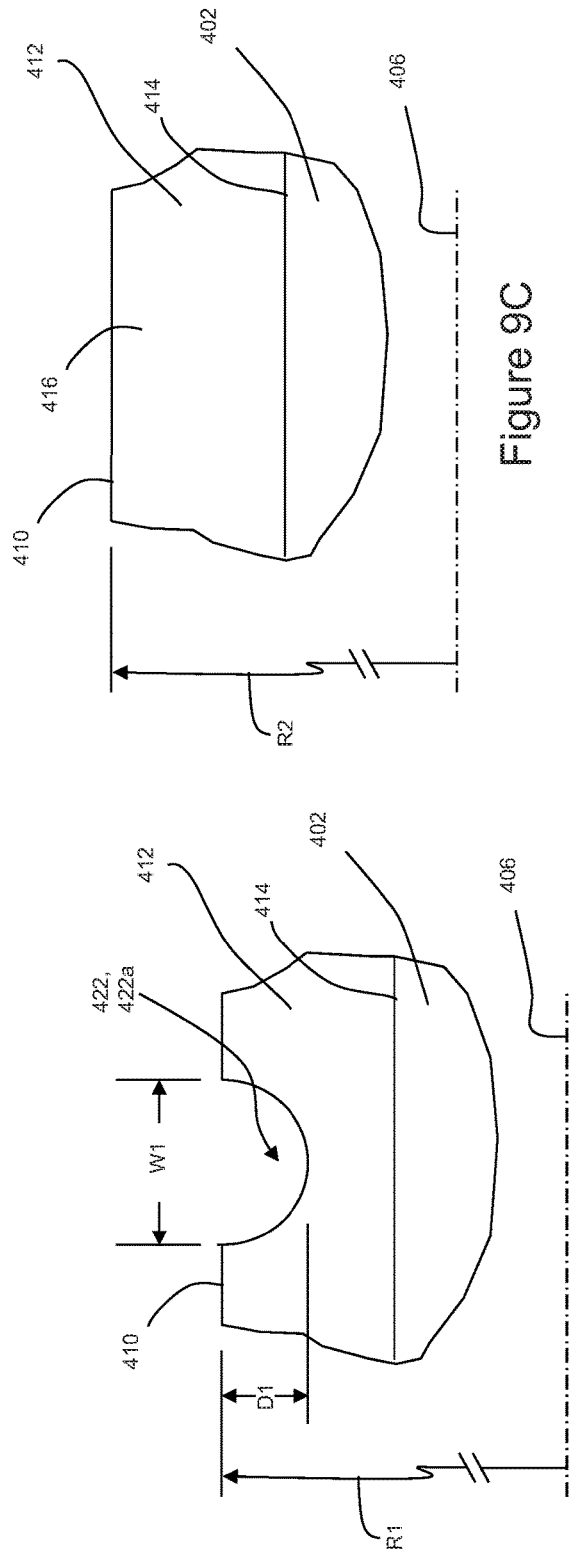
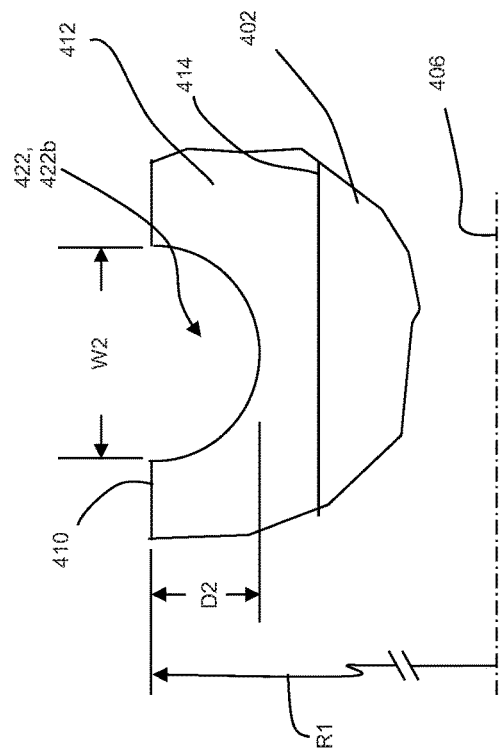
Figure 9A
Figure 9B
Figure 9C

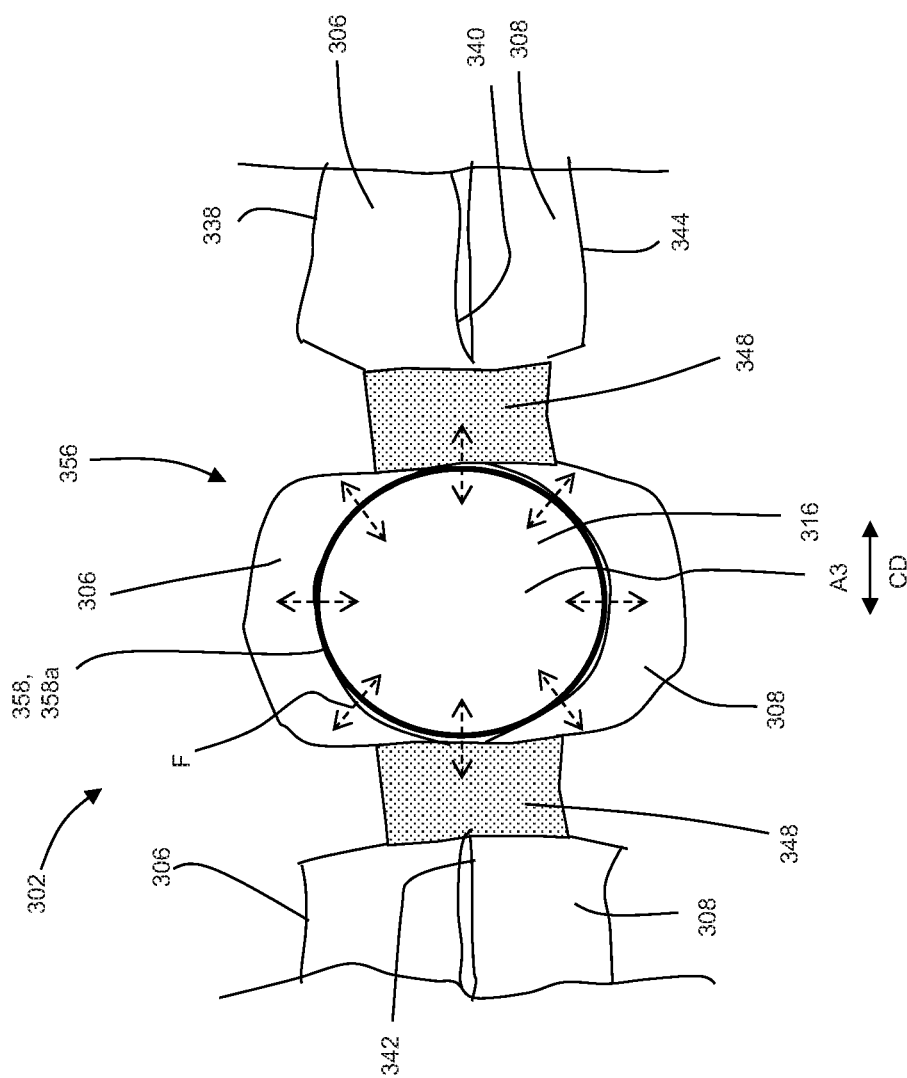

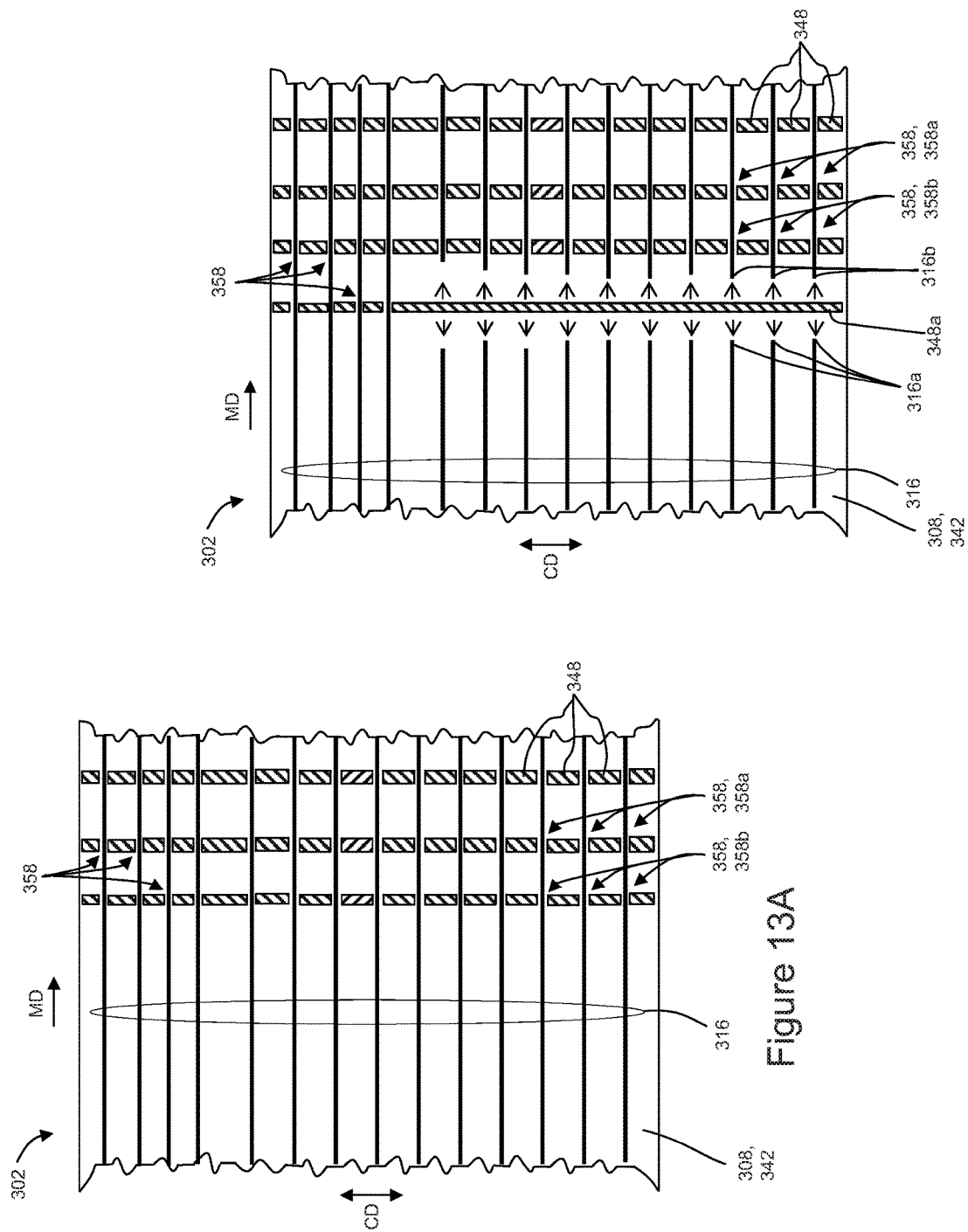

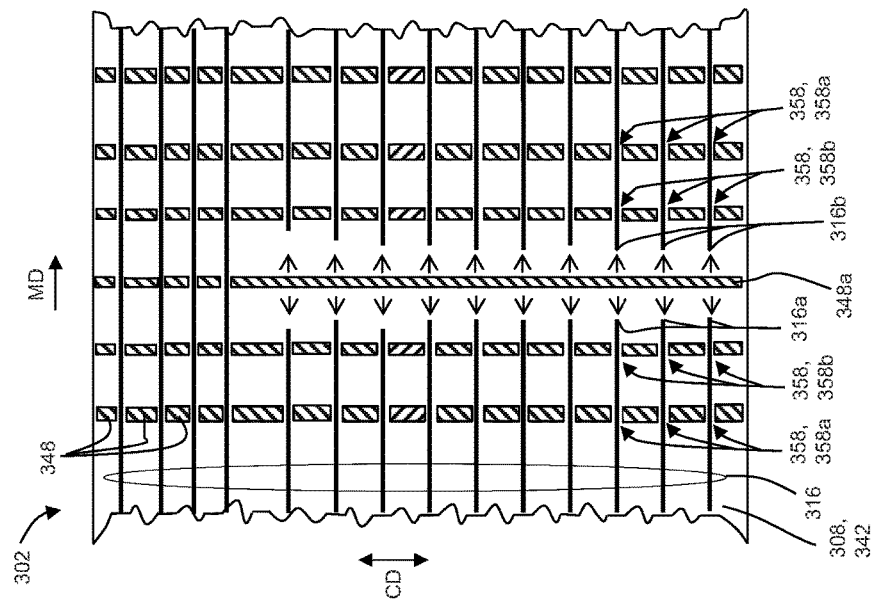
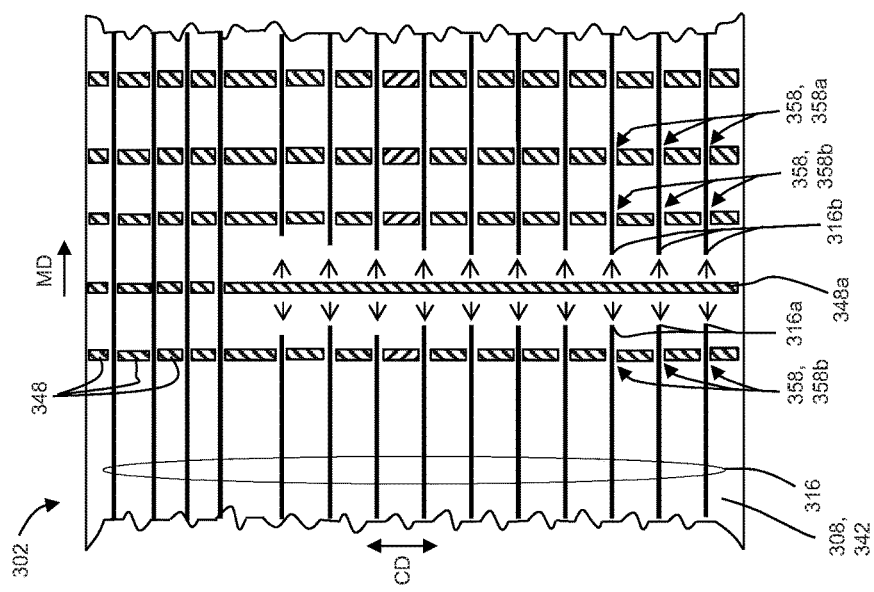

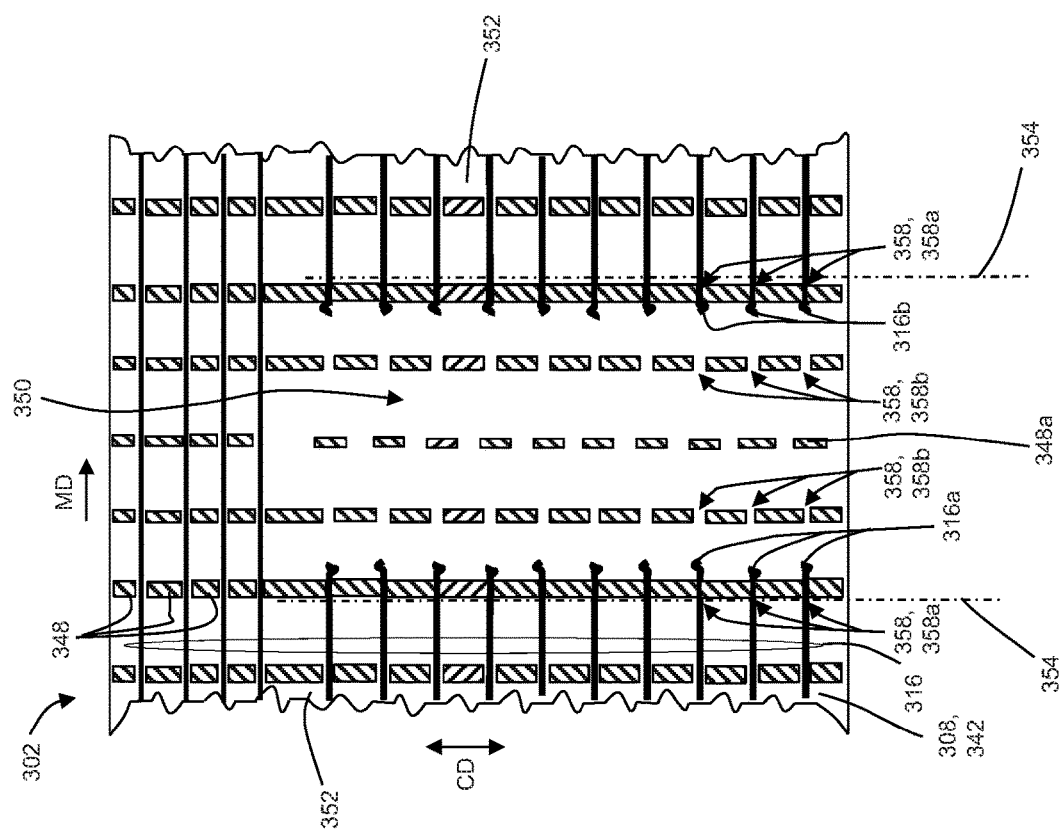

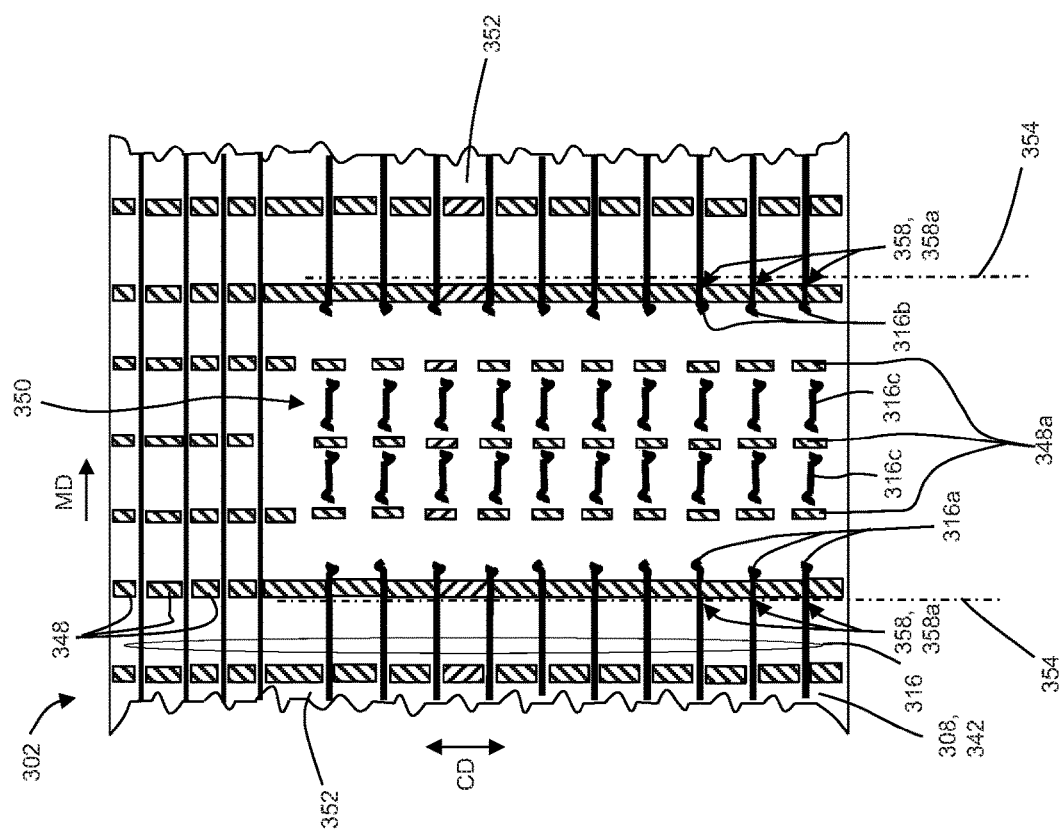

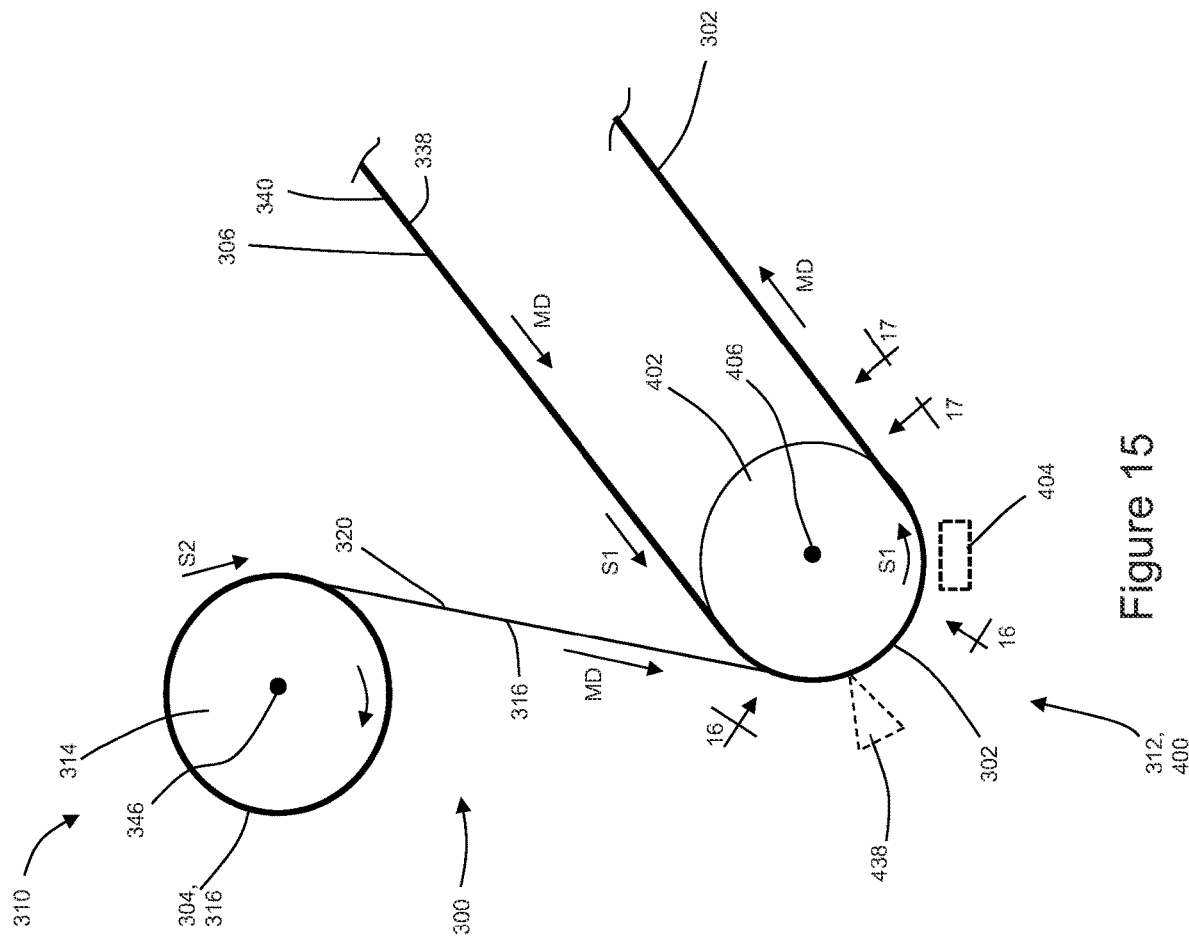

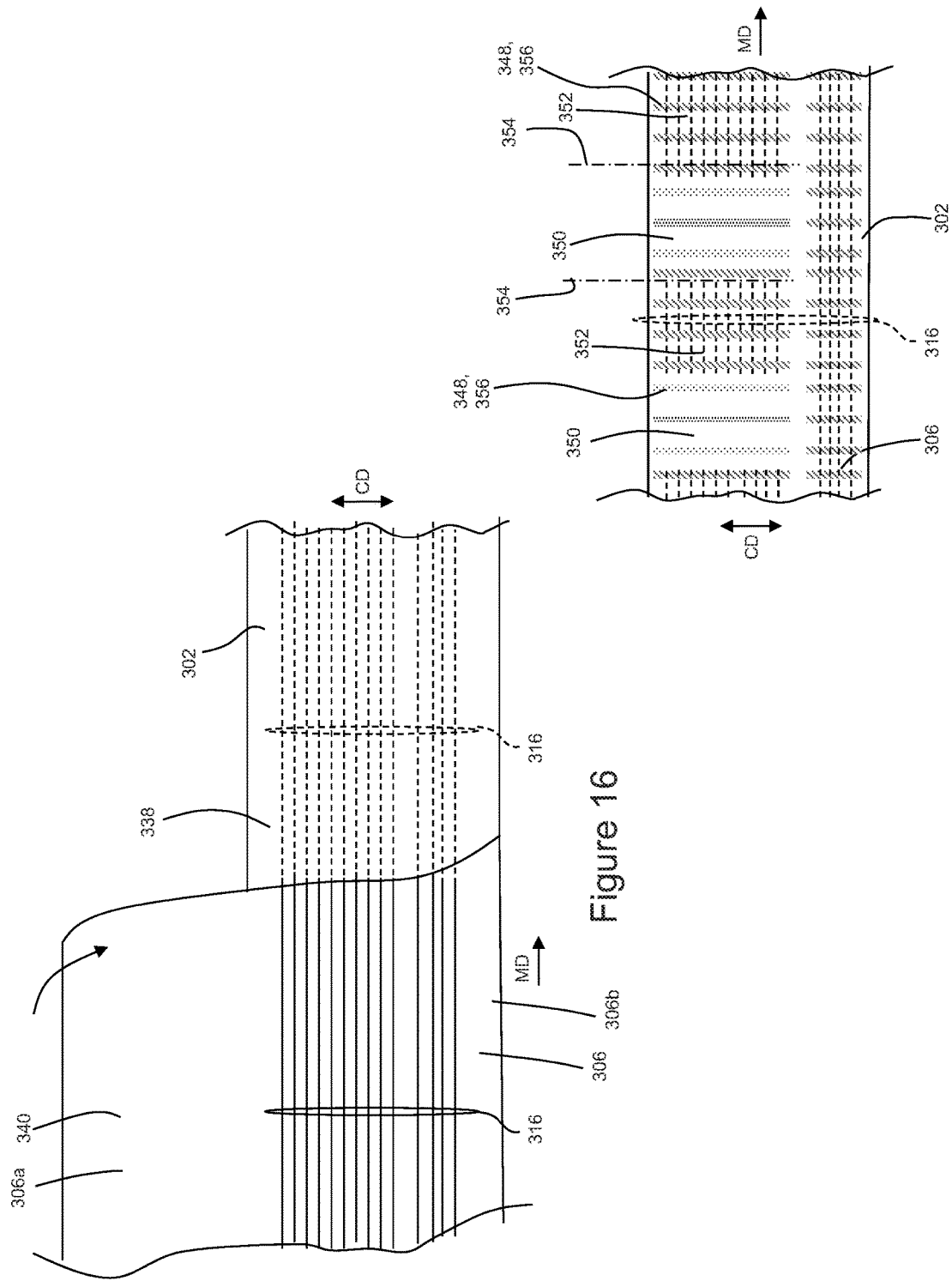

APPARATUSES AND METHODS FOR MAKING ABSORBENT ARTICLES WITH ELASTOMERIC LAMINATES

FIELD OF THE INVENTION

The present disclosure relates to methods for manufacturing absorbent articles, and more particularly, to apparatuses and methods for making elastomeric laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers between the locations where the nonwoven is bonded to the elastic strands, and in turn, forms corrugations. The resulting elastomeric laminate is stretchable to the extent that the corrugations allow the elastic strands to elongate.

In some absorbent article assembly operations, the elasticity of regions of an elastomeric laminate may be removed or deactivated by cutting elastic strands in the regions. For example, some diaper pant embodiments are configured with an absorbent chassis connected with front and back elastic belts, wherein opposing end regions of the front and back belts are connected with each other at side seams. In some configurations, diaper pants may include graphics in certain regions of the belts connect with the absorbent chassis, and the absence of elasticity in such regions may allow for reduced distortion of graphics located in those regions. As such, the elasticity of the front and back belts may be removed in regions where the absorbent chassis connects with the belts. Thus, in some converting configurations adapted to assemble such diaper pants, stretched elastic strands are bonded between two continuous nonwoven webs to form an elastomeric laminate. Regions of the elastic strands may then be intermittently deactivated along the length of the elastomeric laminate by cutting the elastic strands. Subsequent to deactivating the elastic strands, the elastomeric laminate may be subjected to additional handling and converting operations.

In some manufacturing configurations, hot melt adhesives are used to adhere stretched elastic stands to advancing substrates to create elastomeric laminates. However, in attempts to eliminate and reduce the costs and complexities associated with the use of adhesives, some assembly processes may be configured to apply mechanical bonds with heat and pressure to trap the stretched elastic strands between two substrates. Such mechanical bonds may be created, for example, by advancing the substrates and elastic strands between an ultrasonic horn and an anvil, such as disclosed in U.S. Pat. No. 6,291,039 and European Patent Publication No. EP 3 092 997 B1.

However, utilizing mechanical bonding techniques to create elastomeric laminates with unbonded regions and subsequently cutting stretched elastic strands in the unbonded regions to create deactivated regions in the elastomeric laminates may present certain challenges. For example, the ends of the cut elastic stands may snap back in an uncontrolled fashion and consequently may end up in undesired locations within the elastomeric laminate. In some instances, ends of cut elastic strands may form of a lump of elastic material within the elastomeric laminate, which may negatively impact comfort and appearance of an assembled product. Consequently, it would be beneficial to provide methods and apparatuses that are configured to assemble elastomeric laminates in such a way to maximize the aesthetic appearance of such laminates when placed in an assembled product and/or reduce handling of the elastomeric laminates after mechanically bonding the elastics therein.

SUMMARY OF THE INVENTION

In one form, a method for making an elastomeric laminate, the method comprising the steps of: rotating a pattern roll about an axis of rotation extending axially in a cross direction, the pattern roll comprising: a bonding surface; discrete first channels in the bonding surface, wherein the discrete first channels are circumferentially spaced apart from each other; and a protuberance extending axially in the cross direction between two of the discrete first channels; providing a pressing surface adjacent the pattern roll; providing an elastic strand, wherein the elastic strand defines a first cross sectional area in an unstretched state; stretching the elastic strand, wherein the stretched elastic strand defines a second cross sectional area that is less than the first cross sectional area; advancing a first substrate and a second substrate with the stretched elastic strand between the first substrate and the second substrate in a machine direction on the pattern roll, wherein the stretched elastic strand extends through at least one discrete first channel; welding the first substrate and the second substrate together between the bonding surface and the pressing surface to create bonds between the first substrate and the second substrate, wherein the bonds are separated from each other in the cross direction by the stretched elastic strand positioned in the at least one discrete first channel to form a first sleeve surrounding the stretched elastic strand, wherein the first sleeve defines a third cross sectional area that is less than the first cross sectional area and equal to or greater than the second cross sectional area; compressing the first substrate, the second substrate, and the elastic strand between the pressing surface and the protuberance to sever the stretched elastic strand, wherein the severed elastic strand retracts and expands to create a frictional lock between the first sleeve and the severed elastic strand.

In another form, a method for making absorbent articles, the method comprising the steps of: rotating a pattern roll about an axis of rotation extending axially in a cross direction, the pattern roll comprising: a bonding surface; discrete first channels in the bonding surface, wherein the discrete first channels are spaced apart from each other circumferentially and in the cross direction; and a protuberance extending axially in the cross direction between two of the discrete first channels; providing a pressing surface adjacent the pattern roll; providing elastic strands, wherein each elastic strand defines a first cross sectional area in an unstretched state; stretching the elastic strands, wherein each stretched elastic strand defines a second cross sectional area that is less than the first cross sectional area; forming an elastomeric laminate by positioning the stretch elastic strands between a first substrate and a second substrate, wherein the stretched elastic strands are separated from each other in the cross direction; advancing the elastomeric laminate in a machine direction on the pattern roll, wherein the stretched elastic strands extend through respective discrete first channels; welding the first substrate and the second substrate together between the bonding surface and the pressing surface to form bonds between the first substrate and the second substrate, wherein the bonds are separated from each other in the cross direction by the stretched elastic strands positioned in the discrete first channels to form first sleeves surrounding the stretched elastic strands, wherein each first sleeve defines a third cross sectional area that is less than the first cross sectional area and equal to or greater than the second cross sectional area; and forming a deactivated region in the elastomeric laminate positioned along the machine direction between elasticized regions by compressing the first substrate, the second substrate, and at least one elastic strand between the pressing surface and the protuberance to sever the at least one stretched elastic strand, wherein the at least one severed elastic strand retracts and expands to create a frictional lock between the first sleeve and the at least one severed elastic strand.

In yet another form, an apparatus for making an elastomeric substrate, the apparatus comprising: a pattern roll adapted to rotate about an axis of rotation extending axially in a cross direction, the pattern roll comprising: a bonding surface positioned at a first radial distance R1 from the axis of rotation; discrete first channels in the bonding surface, wherein the discrete first channels are spaced apart from each other circumferentially and in the cross direction, the first channels comprising a first width W1 extending axially along the axis of rotation and comprising a first depth D1 extending radially inward from the bonding surface; and a protuberance extending axially along the axis of rotation between two of the discrete first channels, wherein the protuberance extends radially outward from the axis of rotation to a second radial distance R2 wherein R2>(R1−D1); and an ultrasonic horn comprising an energy transfer surface; the ultrasonic horn positioned adjacent the pattern roll to define a nip between the pattern roll and the energy transfer surface.

BRIEF DESCRIPTION OF THE DRAWINGS

FIG. 1A is a front perspective view of a diaper pant.
FIG. 2 is a partially cut away plan view of the diaper pant shown in FIGS. 1A and 1B in a flat, uncontracted state.
FIG. 3A is a cross-sectional view of the diaper pant of FIG. 2 taken along line 3A-3A.
FIG. 3B is a cross-sectional view of the diaper pant of FIG. 2 taken along line 3B-3B.
FIG. 4 shows an example of an empty beam having two side plates connected with opposing end portions of a mandrel core.
FIG. 6 is a view of the converting apparatus of FIG. 5 taken along line 6-6.
FIG. 9A is a sectional view of a first channel on the pattern roll of FIG. 8 taken along line 9A-9A.
FIG. 9B is a sectional view of a second channel on the pattern roll of FIG. 8 taken along line 9B-9B.
FIG. 9C is a sectional view of a protuberance on the pattern roll of FIG. 8 taken along line 9C-9C.
FIG. 12B is a sectional view of the elastic strand, bonds, first substrate, and second substrate of FIG. 11B taken along line 12B-12B.
FIG. 13A shows a detailed view of an elastomeric laminate from FIGS. 5 and 6 advancing from the nip between the pattern roll and pressing surface with the first substrate cut-away to illustrate example bond configurations and stretched elastic strands.
FIG. 13B shows a detailed view of an elastomeric laminate from FIG. 13A continuing to advance from the nip between the pattern roll and pressing surface to illustrate stretched elastic strands having been severed between the protuberance and the pressing surface.

FIG. 13C shows a detailed view of an elastomeric laminate from FIG. 13B continuing to advance from the nip between the pattern roll and pressing surface to illustrate retracting elastic strands after having been severed.

FIG. 13D shows a detailed view of an elastomeric laminate from FIG. 13C continuing to advance from the nip between the pattern roll and pressing surface to illustrate additional bonds having been applied.

FIG. 14A shows a detailed view of an elastomeric laminate illustrating severed elastic strands having retracted to bond regions and showing examples of discrete bonds created by the protuberance in the deactivated region of the elastomeric laminate.

FIG. 14B shows a detailed view of an elastomeric laminate illustrating severed elastic strands having been cut into discrete pieces in the deactivated region of the elastomeric laminate.

FIG. 15 is a schematic side view of an additional configuration of a converting apparatus adapted to manufacture an elastomeric laminate.

FIG. 16 is a view of the converting apparatus of FIG. 15 taken along line 16-16.

FIG. 17 is a view of the converting apparatus of FIG. 15 taken along line 17-17.

DETAILED DESCRIPTION OF THE INVENTION

Figure 1B:
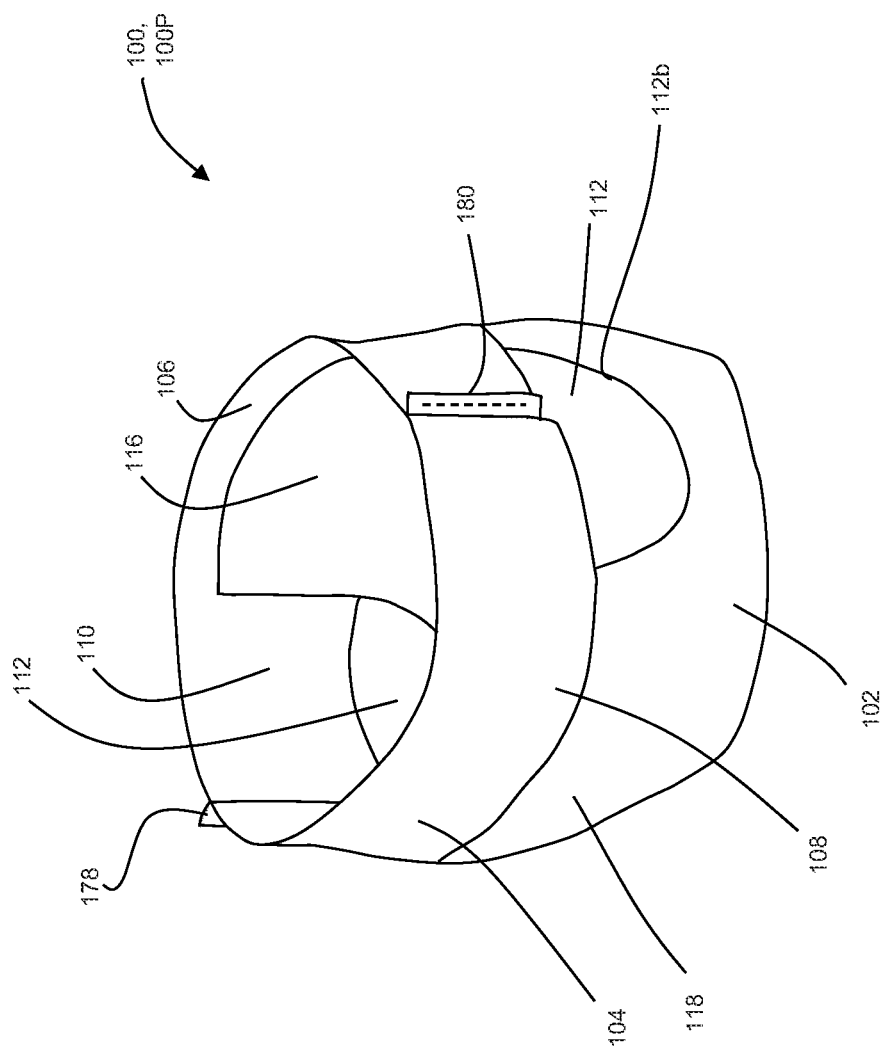
FIG. 1B is a rear perspective view of a diaper pant.

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897,545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

The present disclosure relates to methods and apparatuses for manufacturing absorbent articles, and in particular, for making elastomeric laminates with deactivated regions that may be used as components of absorbent articles. The methods and apparatuses according to the present disclosure may be configured with a pattern roll and a pressing surface adjacent the pattern roll. The pattern roll may be adapted to rotate about an axis of rotation extending axially in a cross direction, and the pressing surface may be configured as an energy transfer surface of an ultrasonic horn. The pattern roll may include a bonding surface and discrete first channels in the bonding surface, wherein the discrete first channels are circumferentially spaced apart from each other. The pattern roll may also include a protuberance extending axially in the cross direction between two of the discrete first channels. As discussed in more detail below, the assembly process utilizes elastic strands that define a first cross sectional area in an unstretched state, and the elastic strands are stretched to define a second cross sectional area that is less than the first cross sectional area. The first and second substrates with the stretched elastic strands therebetween advance in a machine direction on the pattern roll, wherein stretched elastic strands extend through the discrete first channels. As the pattern roll rotates, the first substrate and the second substrate are welded together between the bonding surface and the pressing surface to create bonds between the first and second substrates. The bonds are separated from each other in the cross direction by the stretched elastic strands positioned in respective discrete first channels to form first sleeves surrounding the stretched elastic strands. The first sleeves may each define a cross sectional area that is less than the first cross sectional area and equal to or greater than the second cross sectional area. As the pattern roll continues to rotate, the first substrate, the second substrate, and one or more stretched elastic strands are compressed between the pressing surface and the protuberance to sever the one or more stretched elastic strands to create deactivated regions in the elastomeric laminate. In turn, the one or more severed elastic strands retract and expand to create a frictional lock between the first sleeves and the one or more severed elastic strands. As such, the frictional lock prevents the severed elastic strand from continuing to retract.

As discussed in more detail below, the processes and apparatuses herein may also be configured to help prevent ends of the severed elastic strands from snapping back or retracting in an uncontrolled fashion. For example, during the assembly process, the first substrate, the second substrate, and the stretched elastic strands may be wrapped on the rotating pattern roll. In turn, tension exerted on the first and second substrates force the substrates against the pattern roll, and thus, may help to press and hold the stretched elastic strands in position between the first and second substrates. Thus, as the stretched elastic strands are severed, the ends of the severed elastic strands may tend to retract or snap back at a relatively slower and/or controlled rate. In some configurations, the pattern roll may include second discrete channels that may be circumferentially positioned between first discrete channels and/or between first discrete channels and the protuberance. The discrete second channels may also be wider and and/or deeper than the first discrete channels. As the pattern roll rotates, the first substrate and the second substrate are welded together between the bonding surface and the pressing surface to create bonds between the first and second substrates, wherein the bonds are separated from each other in the cross direction by the stretched elastic strands positioned in respective second channels to form second sleeves surrounding the stretched elastic strands. The second sleeves may each define a cross sectional area that is greater than the cross sectional area of a first sleeve. Thus, the ends of the severed elastic strands may retract through the second sleeves while at the same time being guided along the machine direction by the second sleeves while retracting.

FIGS. 1A, 1B, and 2 show an example of an absorbent article 100 in the form of a diaper pant 100P that may include components constructed from elastomeric laminates assembled in accordance with the apparatuses and methods disclosed herein. In particular, FIGS. 1A and 1B show perspective views of a diaper pant 100P in a pre-fastened configuration, and FIG. 2 shows a plan view of the diaper pant 100P with the portion of the diaper that faces away from a wearer oriented toward the viewer. The diaper pant 100P includes a chassis 102 and a ring-like elastic belt 104. As discussed below in more detail, a first elastic belt 106 and a second elastic belt 108 are bonded together to form the ring-like elastic belt 104.

With continued reference to FIG. 2, the diaper pant 100P and the chassis 102 each include a first waist region 116, a second waist region 118, and a crotch region 119 disposed intermediate the first and second waist regions. The first waist region 116 may be configured as a front waist region, and the second waist region 118 may be configured as back waist region. The diaper 100P may also include a laterally extending front waist edge 121 in the front waist region 116 and a longitudinally opposing and laterally extending back waist edge 122 in the back waist region 118. To provide a frame of reference for the present discussion, the diaper 100P and chassis 102 of FIG. 2 are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, and 2, the diaper pant 100P may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100P may also include other features, such as leg elastics and/or leg cuffs to enhance the fit around the legs of the wearer.

As shown in FIG. 2, the periphery of the chassis 102 may be defined by a first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100P is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100P may include a backsheet 136. The backsheet 136 may also define the outer surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about 0.012 mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100P may include a topsheet 138. The topsheet 138 may also define all or part of the inner surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545,197; and 6,107,539.

As mentioned above, the diaper pant 100P may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/0097895 A1.

As previously mentioned, the diaper 100P may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIG. 2, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 118 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b, the inner laterally extending edge 109b, and the second longitudinal or left side edge 130 of the chassis 102. The outer laterally extending edges 107a, 109a may also define the front waist edge 121 and the laterally extending back waist edge 122 of the diaper pant 100P. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films;

woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107b, 109b.

As previously mentioned, apparatuses and methods according to the present disclosure may be utilized to produce elastomeric laminates that may be used to construct various types of absorbent article components, such as elastic belts, leg cuffs, and the like. For example, FIGS. 4-17 show various aspects of converting apparatuses 300 adapted to manufacture elastomeric laminates 302. As described in more detail below, the converting apparatuses 300 operate to advance a continuous length of elastic material 304, a continuous length of a first substrate 306, and a continuous length of a second substrate 308 along a machine direction MD. It is also to be appreciated that in some configurations, the first substrate and second substrate 306, 308 herein may be defined by two discrete substrates or may be defined by folded portions of a single substrate. The apparatus 300 stretches the elastic material 304 and joins the stretched elastic material 304 with the first and second substrates 306, 308 to produce an elastomeric laminate 302. Although the elastic material 304 is illustrated and referred to herein as strands 316, it is to be appreciated that elastic material 304 may include one or more continuous lengths of elastic strands, ribbons, and/or films.

As discussed in more detail below, the converting apparatuses 300 may include metering devices arranged along a process machine direction MD, wherein the metering devices may be configured to stretch the advancing elastic material and/or join stretch elastic material with one or more advancing substrates. In some configurations, an upstream metering device may comprise an overend unwind device and/or a beam of elastic strands wound thereon. During operation, elastic material may advance in a machine direction from an upstream metering device to a downstream metering device to be joined with one or more advancing substrates to form an elastomeric laminate. The elastomeric laminate is partially wrapped onto a pattern roll adjacent a pressing surface. The pattern roll rotates and advances the elastomeric laminate between the pattern roll and the pressing surface, wherein bonds are applied to the first substrate and the second substrate to secure discrete lengths of the stretched elastic strands between the first and second substrates. The discrete bonds may be arranged intermittently along the machine direction. In some configurations, bonds may be separated from each other in a cross direction by an elastic strand. The pattern roll and pressing surface also operate to remove the elasticity of discrete regions of the elastomeric laminate by cutting one or more elastic strands in the discrete regions. It is to be appreciated that the apparatuses and methods of assembly of elastomeric laminates and absorbent articles described herein and illustrated in the accompanying drawings are non-limiting example configurations. The features illustrated or described in connection with one non-limiting configuration may be combined with the features of other non-limiting configurations. Such modifications and variations are intended to be included within the scope of the present disclosure.

Figure 5:
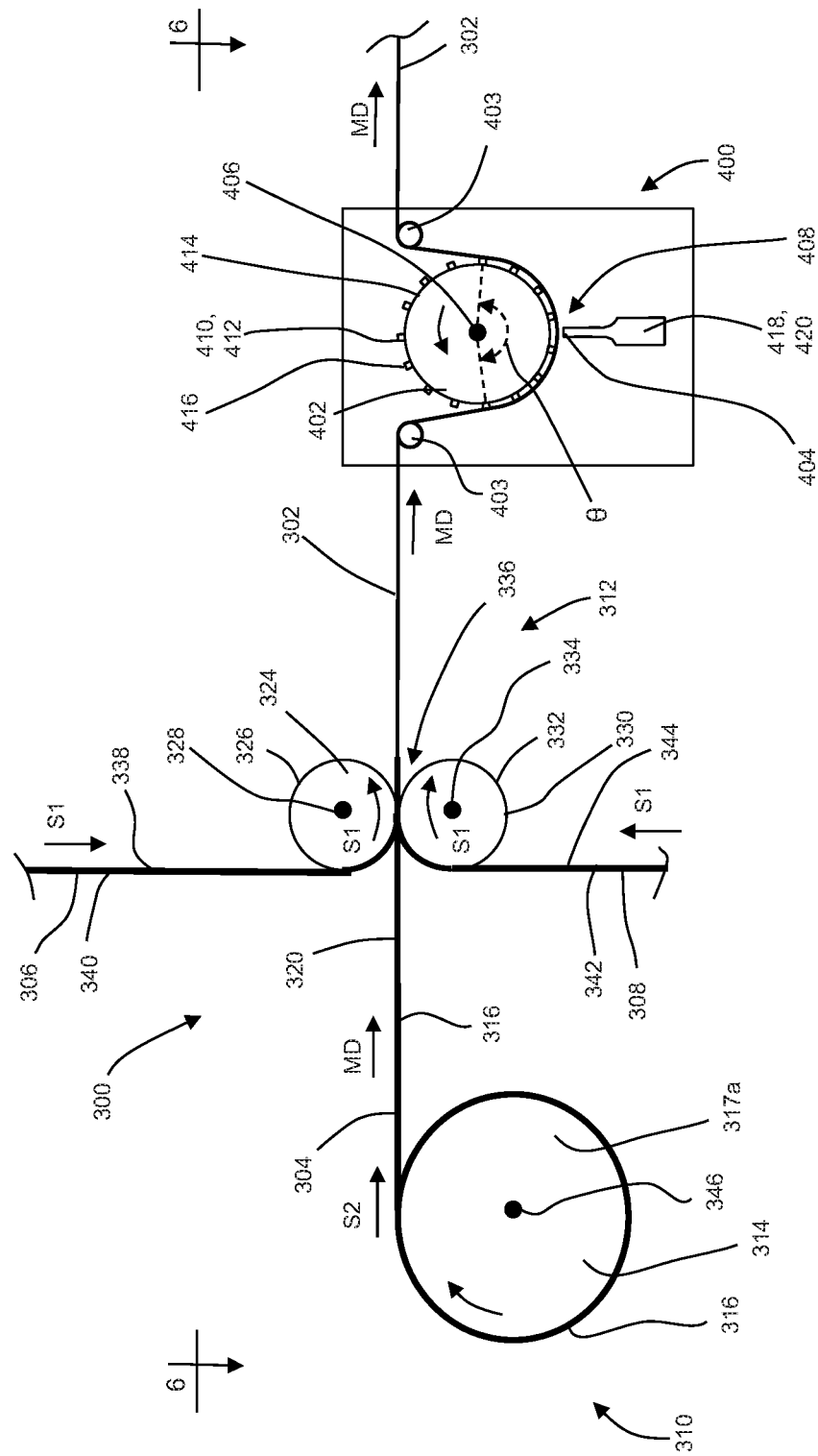
FIG. 5 is a schematic side view of a converting apparatus joining stretched elastic strands between a first substrate and a second substrate.

As shown in FIGS. 5 and 6, a converting apparatus 300 for producing an elastomeric laminate 302 may include a first metering device 310 and a second metering device 312. The first metering device 310 may be configured as a beam 314 with a plurality of elastic strands 316 wound thereon. FIG. 4 shows an example of an empty beam 314 that includes two side plates 317a, 317b that may be connected with opposing end portions of a mandrel core 318, wherein elastic strands may be wound onto the mandrel core 318. It is to be appreciated that beams of various sizes and technical specifications may be utilized in accordance with the methods and apparatuses herein, such as for example, beams that are available from ALUCOLOR Textilmaschinen, GmbH. During operation, the plurality of elastic strands 316 advance in the machine direction MD from the beam 314 to the second metering device 312. In addition, the plurality of elastic strands 316 may be stretched along the machine direction MD between the beam 314 and the second metering device 312. The stretched elastic strands 316 are also joined with a first substrate 306 and a second substrate 308 at the second metering device 312 to produce an elastomeric laminate 302.

It is to be appreciated that the beam 314 may be configured in various ways and with various quantities of elastic strands. Example beams, also referred to as warp beams, that may be used with the apparatus and methods herein are disclosed in U.S. Pat. Nos. 4,525,905; 5,060,881; and 5,775,380; and U.S. Patent Publication No. 2004/0219854 A1. Although FIG. 6 shows fourteen elastic strands 316 advancing from the beam 314, it is to be appreciated that the apparatuses herein may be configured such that more or less than fourteen elastic strands 316 advance from the beam 314. In some configurations, the elastic strands 316 advancing from the beam 314 may include from about 100 to about 2000 strands, specifically reciting all 1 strand increments within the above-recited range and all ranges formed therein or thereby. In some configurations, the elastic strands 316 may be separated from each other by about 0.5 mm to about 4 mm in the cross direction, specifically reciting all 0.1 mm increments within the above-recited range and all ranges formed therein or thereby. As discussed herein, the elastics in the plurality of elastic strands may be pre-strained prior to joining the elastic strand to the first or second substrate layers 306, 308. In some configurations, the elastic may be pre-strained from about 75% to about 300%, specifically reciting all 1% increments within the above-recited range and all ranges formed therein or thereby. It is also to be appreciated that one or more beams of elastics may be arranged along the cross direction CD of a converting process and/or arranged along a machine direction MD in various different portions of a converting process. It is also to be appreciated that the beam 314 can be connected with one or more motors, such as servo motors, to drive and control the rotation of the beam 314. It is to be appreciated that in some configurations, the elastic strands 316 may be supplied on the beam 314 in a stretched state, and as such, may not require additional stretching (or may require relatively less additional stretching) before being combined with the first substrate 306 and/or the second substrate 308. In some configurations, an elastic strand 316 may be drawn from a single roll utilizing a rolling unwind, such as for example, available from Overend Technologies, Inc.

In some configurations, one or more of the elastic strands 316 advancing from the beam 314 may also include a spin finish 320 located on outer surfaces of the elastics strands. It is to be appreciated the elastic strands 316 may include various types of spin finish 320, also referred herein as yarn finish, configured as coating on the elastic strands 316 that may be intended to help prevent the elastics strands from adhering to themselves, each other, and/or downstream handling equipment. In some configurations, a spin finish may include various types of oils and other components, such as disclosed for example in U.S. Pat. Nos. 8,377,554; 8,093,161; and 6,821,301. In some configurations, a spin finish may include various types of silicone oils, such as for example, polydimethylsiloxane. In some configurations, a spin finish may include various types of mineral oils. It is to be appreciated that the amount of spin finish applied to elastic strands may be optimized depending on the process configuration in which the elastic strands may be used. For example, in process configurations wherein elastic strands have limited contact or do not contact downstream handling equipment, such as idlers, the amount of spin finish may be selected to help prevent the elastics strands from adhering to themselves and/or each other while wound on a beam without regard to whether elastic strands would adhere to downstream handling equipment. As such, it is to be appreciated that the elastic strands herein may include various amounts of spin finish that may be expressed in various ways. For example, a quantity of 10 grams of spin finish per 1 kilogram of elastic strand may be expressed as 1% spin finish. In some configurations, an elastic strand may include about 0.1% spin finish. In some configurations, a strand may include from about 0.01% to about 10% spin finish, specifically reciting all 0.01% increments within the above-recited range and all ranges formed therein or thereby.

As discussed above, the elastic strands 316 advancing from the rotating beam 314 may also include a spin finish 320, and as such, the apparatuses herein may be configured to bond the elastic strands 316 between the substrates 306, 308 without having to remove the spin finish 320 before joining the elastic strands 316 with the substrates 306, 308. It is also to be appreciated that the methods and apparatuses herein may also be configured to remove the spin finish 320 from the elastic strands 316. Examples of spin finish removal processes and apparatuses are disclosed in U.S. Provisional Patent Application No. 62/483,965, which is incorporated by reference herein. In addition, the elastomeric laminates 302 herein may be constructed with or without adhesives between the first and second substrates 306, 308. In addition, it is to be appreciated that the bonding methods and apparatuses herein may be utilized in conjunction with other bonding methods and apparatuses, such as disclosed in U.S. Patent Application Nos. 62/436,589; 62/553,149; and 62/553,171, which are incorporated by reference herein.

Although the elastomeric laminate assembly process may utilize elastic strands supplied from a beam, it is to be appreciated that the elastic strands may also be supplied with various types of elastic unwinder configurations, such as disclosed in U.S. Pat. Nos. 6,676,054; 7,878,447; 7,905,446; and 9,156,648, all of which are incorporated by reference herein.

Referring again to FIGS. 5 and 6, the second metering device 312 may include: a first roller 324 having an outer circumferential surface 326 and that rotates about a first axis of rotation 328, and a second roller 330 having an outer circumferential surface 332 and that rotates about a second axis of rotation 334. The first roller 324 and the second roller 330 rotate in opposite directions, and the first roller 324 is adjacent the second roller 330 to define a nip 336 between the first roller 324 and the second roller 330. The first roller 324 rotates such that the outer circumferential surface 326 has a surface speed S1, and the second roller 330 may rotate such that the outer circumferential surface 332 has the same, or substantially the same, surface speed S1.

With continued reference to FIGS. 5 and 6, the first substrate 306 includes a first surface 338 and an opposing second surface 340, and the first substrate 306 advances to the first roller 324. In particular, the first substrate 306 advances at speed S1 to the first roller 324 where the first substrate 306 partially wraps around the outer circumferential surface 326 of the first roller 324 and advances through the nip 336. As such, the first surface 338 of the first substrate 306 travels in the same direction as and in contact with the outer circumferential surface 326 of the first roller 324. In addition, the second substrate 308 includes a first surface 342 and an opposing second surface 344, and the second substrate 308 advances to the second roller 330. In particular, the second substrate 308 advances at speed S1 to the second roller 330 where the second substrate 308 partially wraps around the outer circumferential surface 332 of the second roller 330 and advances through the nip 336. As such, the second surface 344 of the second substrate 308 travels in the same direction as and in contact with the outer circumferential surface 332 of the second roller 330.

Still referring to FIGS. 5 and 6, the beam 314 includes elastic strands 316 wound thereon, and the beam 314 is rotatable about a beam rotation axis 346. In some configurations, the beam rotation axis 346 may extend in the cross direction CD. As the beam 314 rotates, the elastic strands 316 advance from the beam 314 at a speed S2 with the elastic strands 316 being spaced apart from each other in the cross direction CD. From the beam 314, the elastic strands 316 advance in the machine direction MD to the nip 336. In some configurations, the speed S2 is less than the speed S1, and as such, the elastic strands 316 are stretched in the machine direction MD. In turn, the stretched elastic strands 316 advance through the nip 336 between the first and second substrates 306, 308 such that the elastic strands 316 are joined with the second surface 340 of the first substrate 306 and the first surface 342 of the second substrate 308 to produce a continuous length of elastomeric laminate 302.

With continued reference to FIGS. 5 and 6, the advancing elastic strands 316 may be joined with the first substrate 306 and the second substrate 308 to form the elastomeric laminate 302. The elastomeric laminate 302 may also advance to a bond applicator 400 configured to apply bonds 348 that secure the elastic strands 316 between the first substrate 306 and the second substrate 308. The bond applicator 400 may also be configured to intermittently sever one or more stretched elastic strands 316 to create deactivated regions 350 in the elastomeric laminate 302. As shown in FIG. 6, the deactivated regions 350 may be intermittently spaced between elastomeric regions 352 along the machine direction MD. For the purposes of clarity, dashed lines 354 are shown in FIG. 6 to represent example boundaries between the deactivated regions 350 and the elastomeric regions 352. It is to be appreciated that such boundaries between the deactivated regions 350 and the elastomeric regions 352 can also be curved, angled, and/or straight.

It is to be appreciated that the bond applicator 400 may be configured in various ways, such as with heated or unheated patterned and anvil rolls and/or ultrasonic bonding devices. For example, the bond applicator 400 schematically shown in FIGS. 5 and 6 may include a pattern roll 402 and pressing surface 404 adjacent the pattern roll 402. The pattern roll 402 may be adapted to rotate about an axis of rotation 406 extending axially in the cross direction CD. During operation, the elastomeric laminate 302 may be partially wrapped onto the pattern roll 402. And the pattern roll 402 rotates about the axis of rotation 406 to advance the elastomeric laminate 302 through a nip 408 between the pattern roll 402 and the pressing surface 404. As shown in FIG. 5, the bond applicator 400 may also include one or more rolls 403 that help guide the elastomeric laminate to and from the pattern roll 402. The pattern roll 402 may also comprise one or more bonding surfaces 410 defined by one or more bonding elements 412 extending radially outward from an outer circumferential surface 414. The pattern roll 402 may also comprise a protuberance 416 extending radially outward from the outer circumferential surface 414. As discussed in more detail below, the elastomeric laminate 302 is advanced between the bonding surface 410 and the pressing surface 404 to weld the first substrate 306 and the second substrate 308 together to create bonds 348 between the first substrate 306 and the second substrate 308. And the elastomeric laminate 302 is advanced between the protuberance 416 and the pressing surface 404 to sever one or more elastic strands 316. Thus, as the elastomeric laminate 302 advances through the nip 408, the first substrate 306 and the second substrate 308 are welded together and one or more elastic strands 316 are intermittently severed to create deactivated regions 350 in the elastomeric laminate 302.

As discussed above, during the assembly operation, the elastomeric laminate 302 may be partially wrapped onto the pattern roll 402. As shown in FIG. 5, the extent that the elastomeric laminate 302 wraps around the pattern roll 402 is referred to herein as the wrap angle, θ, and may be expressed in units of degrees. In some configurations, the wrap angle, θ, may be greater than zero degrees and less than or equal to 180 degrees, specifically reciting all 1 degree increments within the above-recited range and all ranges formed therein or thereby. In some configurations, the wrap angle, θ, may be greater 180 degrees.

It is to be appreciated that the pressing surface 404 may be configured in various ways. For example, as shown in FIG. 5, the pressing surface 404 may comprise an energy transfer surface of an ultrasonic bonding device 418. As such, the bond applicator 400 may include a horn 420 and may be configured to impart ultrasonic energy to the combined substrates 306, 308 and elastic strands 316 on the pattern roll 402. The ultrasonic bonding device 418 may apply energy to the horn 420 to create resonance of the horn 420 at frequencies and amplitudes so the horn vibrates rapidly in a direction generally perpendicular to the substrates 306, 308 and elastic strands 316 being advanced past the horn 420 on the pattern roll 402. Vibration of the horn 420 creates bonds 348 and/or bond regions 356 by generating heat to melt and bond the substrates 306, 308 together in areas supported by the bonding surface 410 on the pattern roll 402. Thus, the bonds 348 and/or bond regions 356 may have shapes that correspond with and may mirror shape of the bonding surfaces 410.

It is to be appreciated that aspects of the ultrasonic bonding devices 418 may be configured in various ways, such as for example linear or rotary type configurations, and such as disclosed for example in U.S. Pat. Nos. 3,113,225; 3,562,041; 3,733,238; 5,110,403; 6,036,796; 6,508,641; and 6,645,330. In some configurations, the ultrasonic bonding device 418 may be configured as a linear oscillating type sonotrode, such as for example, available from Herrmann Ultrasonic, Inc. In some configurations, the sonotrode may include a plurality of sonotrodes nested together in the cross direction CD.

Although the bond applicator 400 is shown in FIGS. 5 and 6 as a separate device that is positioned downstream of the second metering device 312, it is to be appreciated that the second metering device 312 may also be configured as the bond applicator 400. As such, the first substrate 306, second substrate 308, and elastic strands 316 may be combined and bonded together at the bond applicator 400 to form the elastomeric laminate 302.

It is to be appreciated that the apparatuses and methods herein may be configured to create various configurations of bonds 348 in the elastomeric laminate 302. For example, as previously mentioned, the pattern roll 402 may include one or more bonding elements 412 protruding radially outward from the pattern roll 402, wherein each bonding element 412 includes a bonding surface 410, such as shown for example in FIGS. 7 and 8. It is to be appreciated that the number, size, and shape of some or all the bonding surfaces 410 and/or bonding elements 412 may be different. In some embodiments, the shape and size of the bonding surface 410 of each bonding element 412 may be identical or substantially identical to each other. In some configurations, the bonding elements 412 and/or bonding surfaces 410 may have a perimeter that defines circular, square, rectangular, elliptical, and various types of other shapes. In some configurations, the pattern roll 402 may include a bonding element 412 with a bonding surface 410 that defines a continuous crossing line pattern and/or various other shapes, such as disclosed in U.S. Pat. No. 9,265,672, which is incorporated by reference herein. It is to be appreciated that the bonding surface 410, such as discussed above, may be flat and/or may also include regions defined by relatively high and relatively low elevations. Thus, such bonding surfaces 410 may create bonds 348 having varying thicknesses across the bond region 356.

Figure 6A:
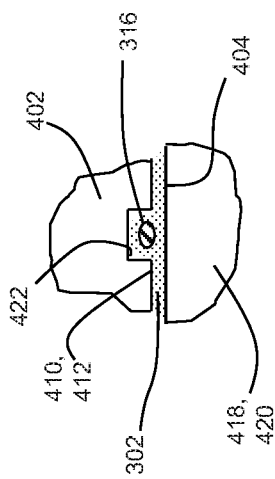
FIG. 6A is a detailed cross sectional view of the elastomeric laminate advancing through the nip between the pattern roll and the pressing surface showing an elastic strand extending through a channel.
Figure 7:
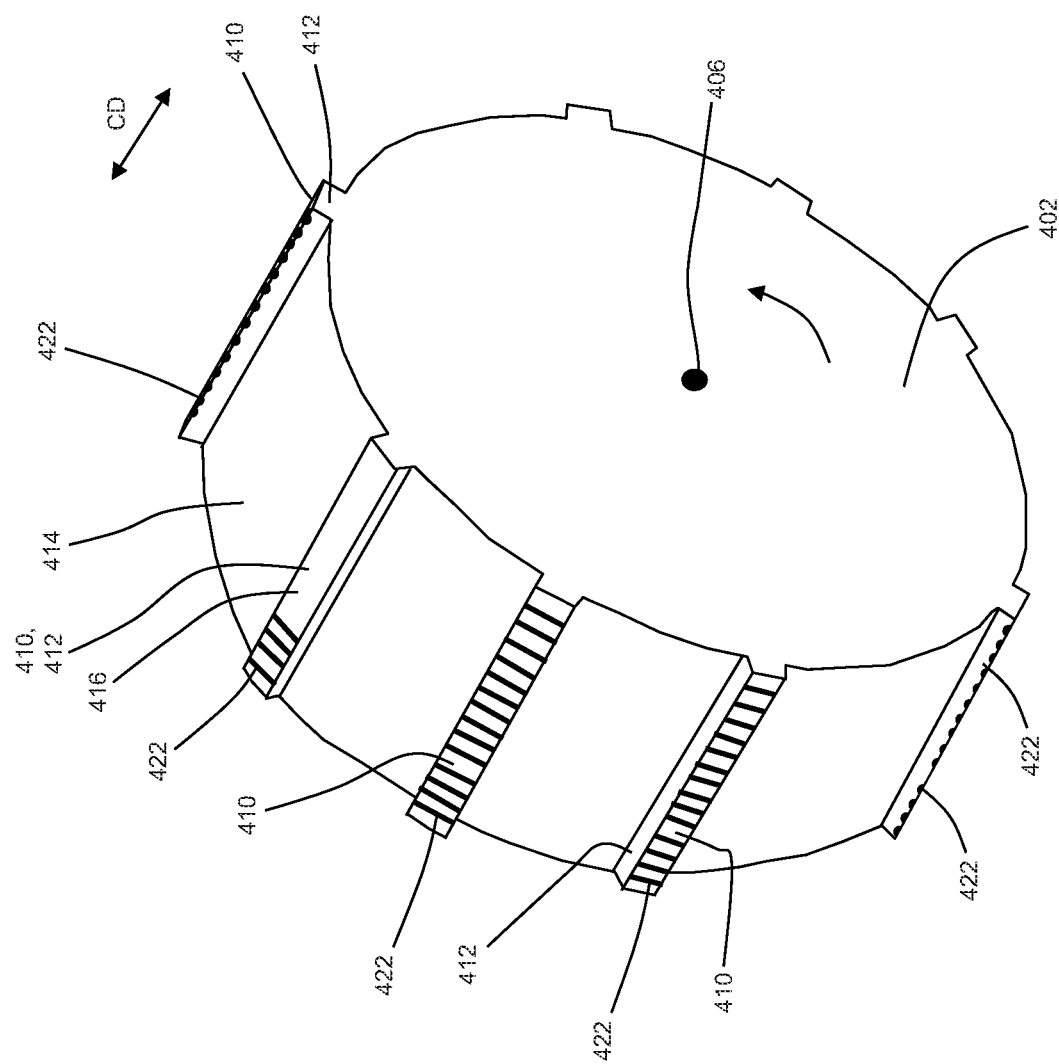
FIG. 7 is a detailed view of an example pattern roll with pluralities of bonding surfaces and a protuberance.
Figure 8:
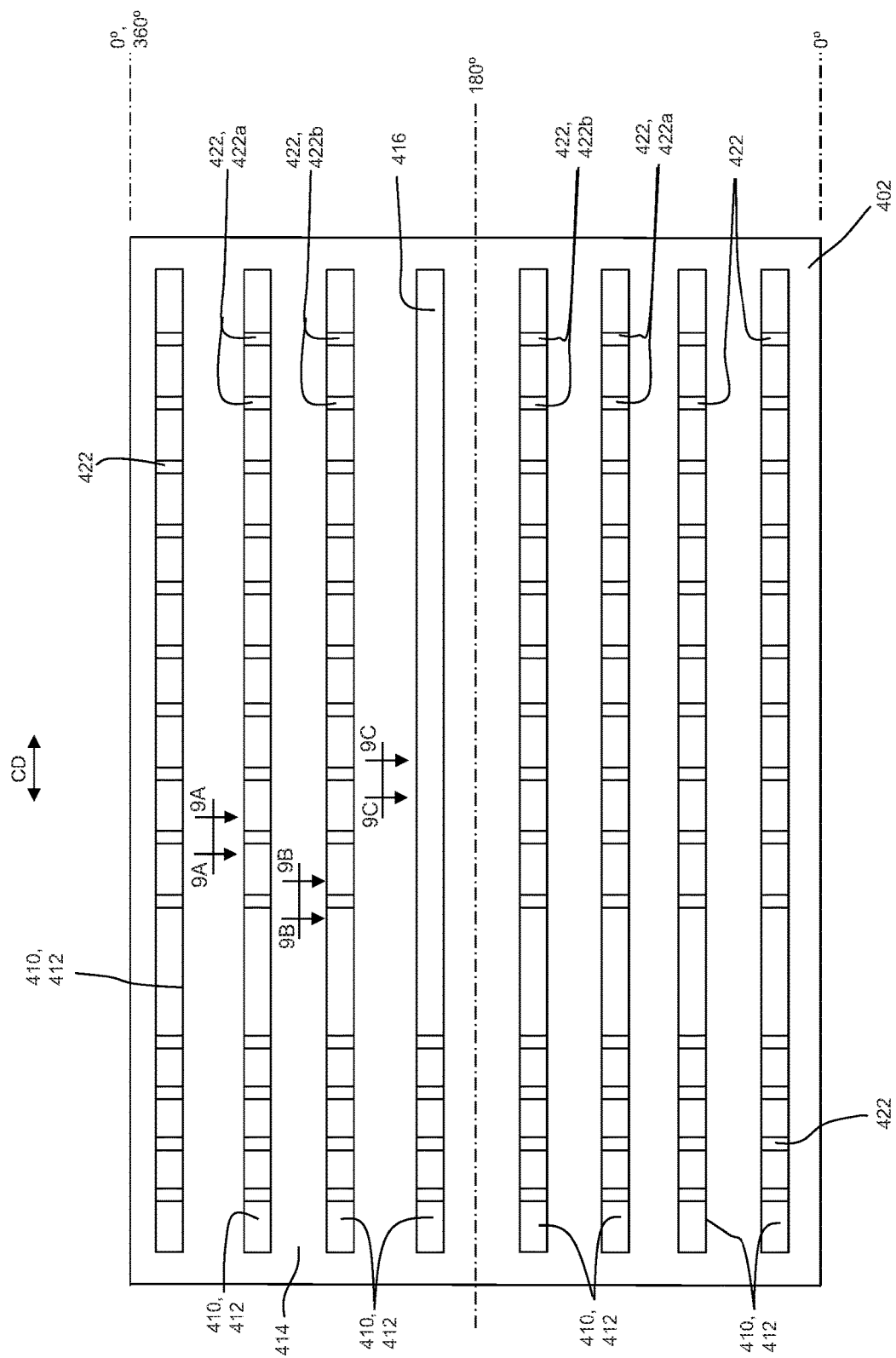
FIG. 8 is a view of an outer circumferential surface of a pattern roll laid out flat and showing pluralities of bonding surfaces and a protuberance.

With continued reference to FIGS. 7 and 8, the pattern roll 402 may also include discrete channels 422 in the bonding surfaces 410. During operation, the first substrate 306 and the second substrate 308 with the stretched elastic strands 316 therebetween may be advanced onto the pattern roll 402, wherein the stretched elastic strands 316 are aligned with and extend through respective channels 422, such as shown in FIG. 6A. As the pattern roll 402 rotates, the first substrate 306 and the second substrate 308 are welded together between the bonding surfaces 410 and the pressing surface 404 to create bonds 348 between the first substrate 306 and the second substrate 308. As discussed below in more detail with reference to FIGS. 11A-12B, the bonds 348 are separated from each other in the cross direction CD by the stretched elastic strands 316 positioned in the channels 422 to form sleeves 358 that surround the stretched elastic strands 316. The inner perimeter of the sleeves 358 may be defined by the first substrate 306, the second substrate 308, and the bonds 348 on opposing sides of the elastic strand 316.

Figure 8A:
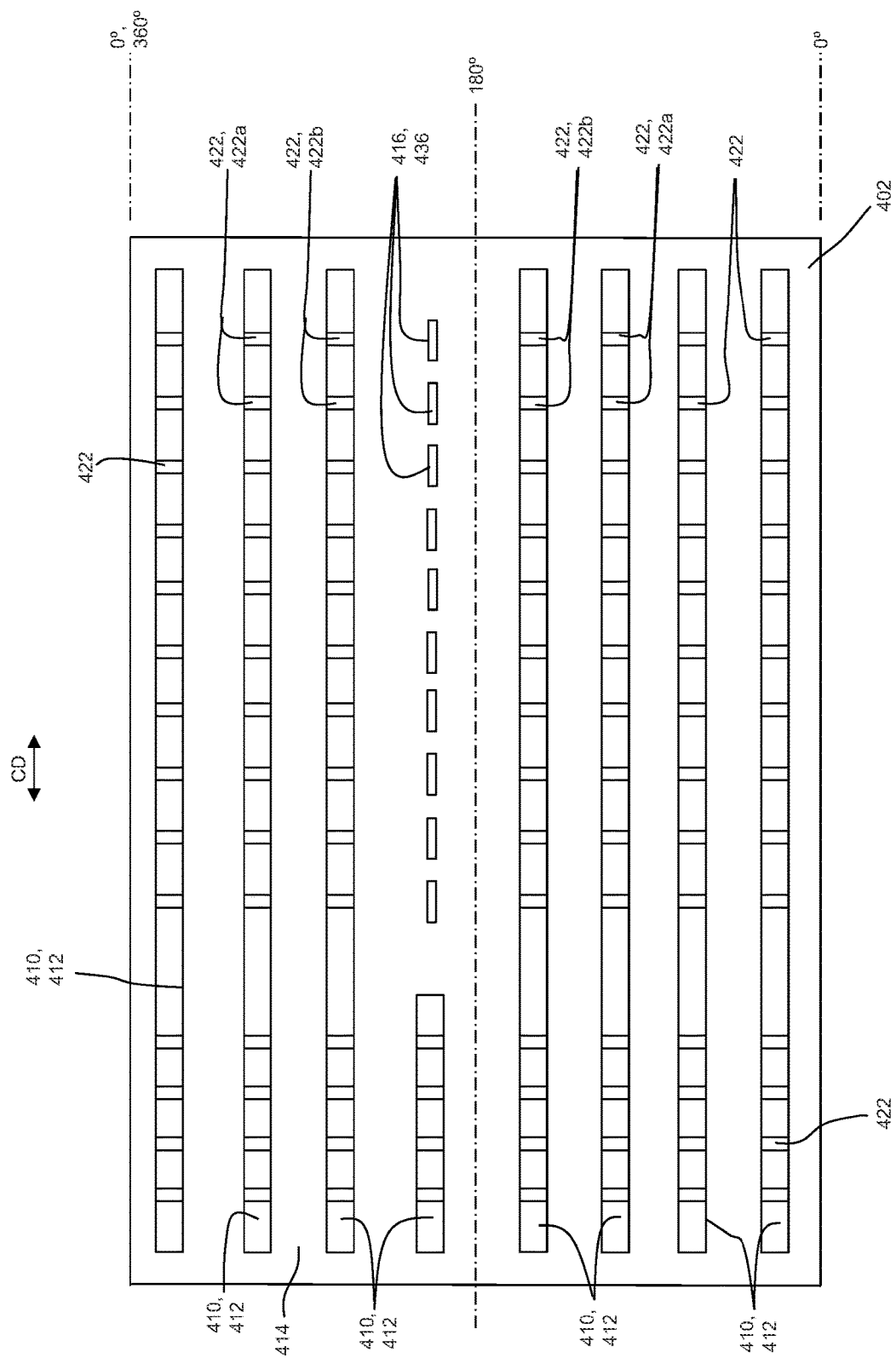
FIG. 8A is a view of an outer circumferential surface of a pattern roll laid out flat and showing a protuberance configured as a plurality of discrete members.

As shown in FIGS. 8, 8A, and 8B, the pattern roll 402 may include first channels 422a and second channels 422b, wherein the first and second channels 422a, 422b may be configured to create sleeves 358 having different sizes. As shown in FIGS. 9A and 9B, the bonding surfaces 410 may be positioned at a first radial distance R1 from the axis of rotation 406. Discrete first channels 422a may be positioned in the bonding surfaces 410 so as to be spaced apart from each other circumferentially and in the cross direction CD. In addition, the first channels 422a may comprise a first width W1 extending axially along the axis of rotation 406 and may comprise a first depth D1 extending radially inward from the bonding surface 410. Discrete second channels 422b may also be positioned in the bonding surfaces 410 so as to be spaced apart from each other circumferentially and in the cross direction CD. The second channels 422b may comprise a second width W2 extending axially along the axis of rotation 406 and may comprise a second depth D2 extending radially inward from the bonding surface 410. In some configurations, the second width W2 may be greater than the first width W1 and/or the second depth D2 may be greater than the first depth D1. In turn, the first channels 422a may be configured to create first sleeves 358a that are sized to secure discrete lengths of the elastic strands 316 in fixed positions with a frictional lock between the first and second substrates 306, 308. In addition, the second channels 422b may be configured to create second sleeves 358b that are sized to allow the elastic strands 316 to move relative to the first and second substrates 306, 308 as the elastic strands 316 stretch and contract along machine direction MD while at the same time holding and/or guiding the elastic strands 316 in desired positions along the cross direction CD.

Figure 10A:
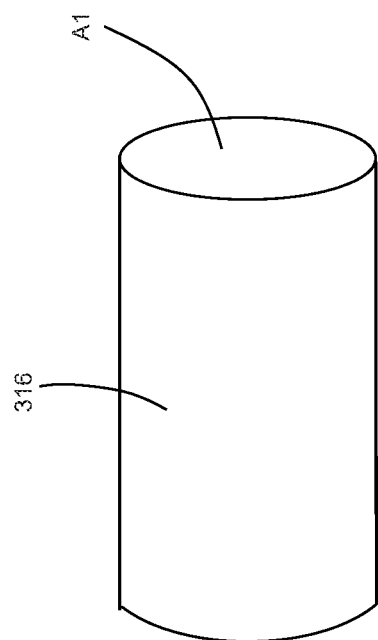
FIG. 10A shows a length of an elastic strand in a relaxed state with a first cross sectional area.
Figure 10B:
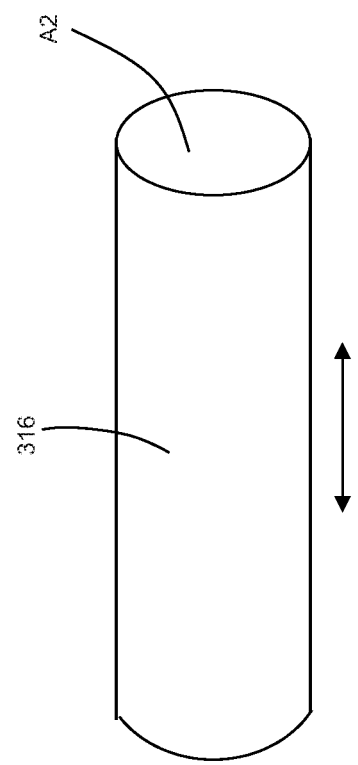
FIG. 10B shows a length of an elastic strand in a stretched state with a second cross sectional area.

As previously mentioned, the pattern roll 402 may include first channels 422a that are sized to create first sleeves 358a that surround discrete lengths of stretched elastic strands 316. In turn, a frictional lock may be applied between a portion of the elastic strand 316 and the first sleeves 358a by releasing tension from the stretched elastic strand 316. The frictional lock acts to hold and/or secure a portion of the elastic strand 316 in a fixed position relative to the first and second substrates 306, 308. For the purposes of a general explanation, FIG. 10A shows a length of an elastic strand 316 in a unstretched or relaxed state, wherein the elastic strand 316 defines a first cross sectional area A1. And FIG. 10B shows a length of the elastic strand 316 from FIG. 10A in a stretched state, wherein the elastic strand 316 defines a second cross sectional area A2 that is less than the first cross sectional area A1. Thus, the cross sectional area of the stretched elastic strand 316 expands when tension is partially or fully released from the stretched elastic strand 316. As discussed in more detail below, the tendency of the cross sectional area of the elastic strand 316 to expand helps create the frictional lock.

Figure 11A:
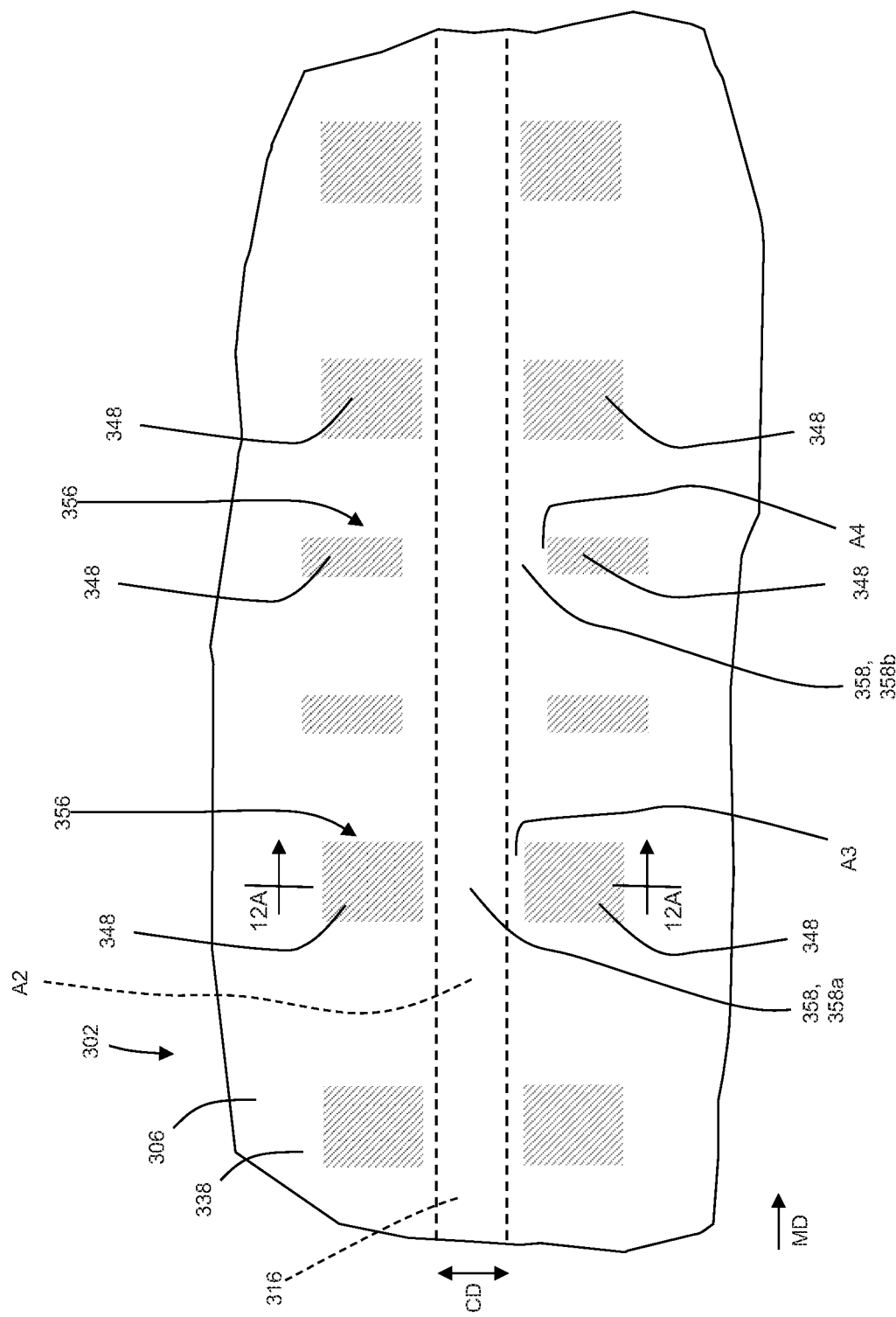
FIG. 11A is a detailed view of an elastic strand in a stretched state bonded between the first and second substrates.
Figure 12A:
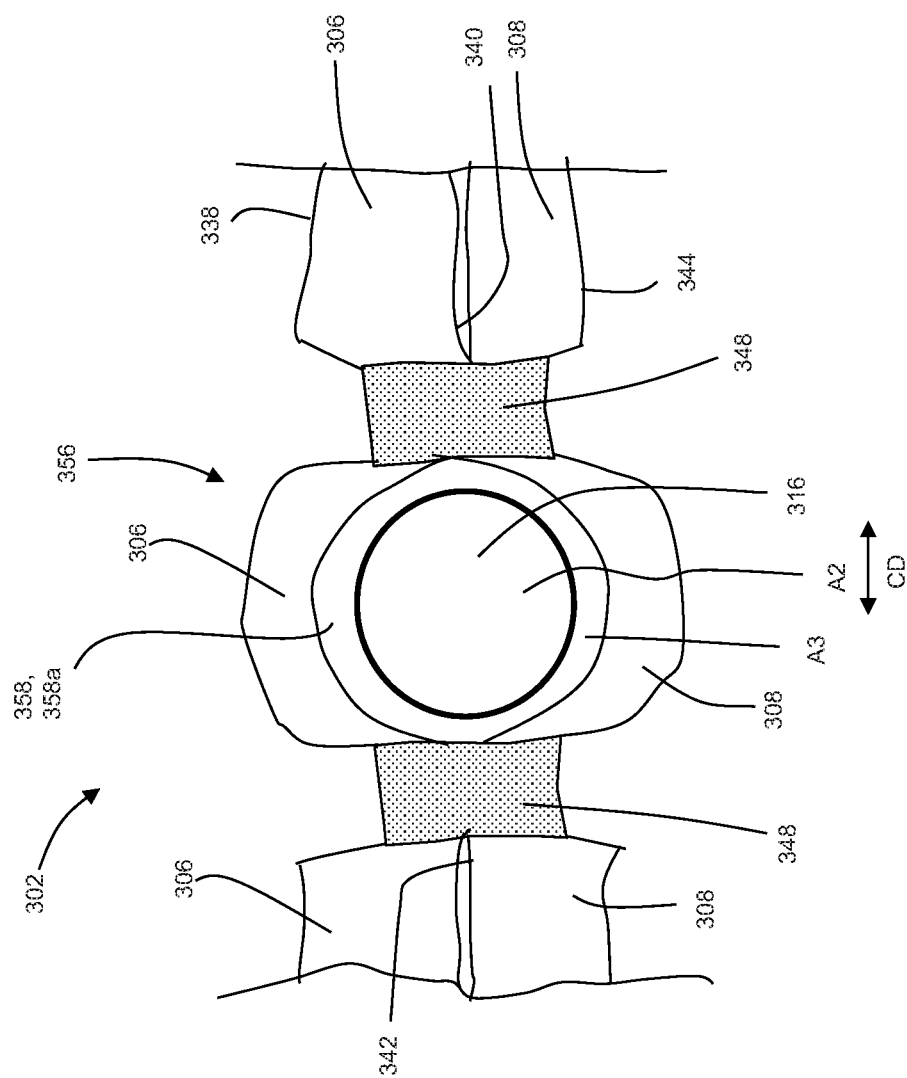
FIG. 12A is a sectional view of the elastic strand, bonds, first substrate, and second substrate of FIG. 11A taken along line 12A-12A.

FIGS. 11A and 12A are detailed views of an elastic strand 316, such as shown in FIG. 6, in a stretched state extending in the machine direction between the first and second substrates 306, 308. During the bonding process, the bond applicator 400 may apply heat and pressure to regions of the first substrate 306 and the second substrate 308 to weld the first and second substrates 306, 308 together with bonds 348. The bonds 348 may be separated from each other in the cross direction CD by the stretched elastic strand 316. In turn, the bonds 348 form sleeves 358 that surround the stretched elastic strands 316. As shown in FIG. 12A, the inner perimeter of the sleeves 358 may be defined by the first substrate 306, the second substrate 308, and the bonds 348 on opposing sides of the elastic strand 316. As discussed above, the first channels 422a in the pattern roll 402 may be configured to create first sleeves 358a to secure discrete lengths of the elastic strands 316 in fixed positions with a frictional lock between the first and second substrates 306, 308. For example, the elastic strand 316 shown in FIGS. 11A and 12A may define a second cross sectional area A2 in a stretched state. The elastic strand 316 may also define a first cross sectional area A1 in a relaxed state, wherein A2 is less than A1. In turn, the first sleeves 358a may define a third cross sectional area A3 that may be greater than or equal to A2, and wherein A3 may be less than A1.

Figure 11B:
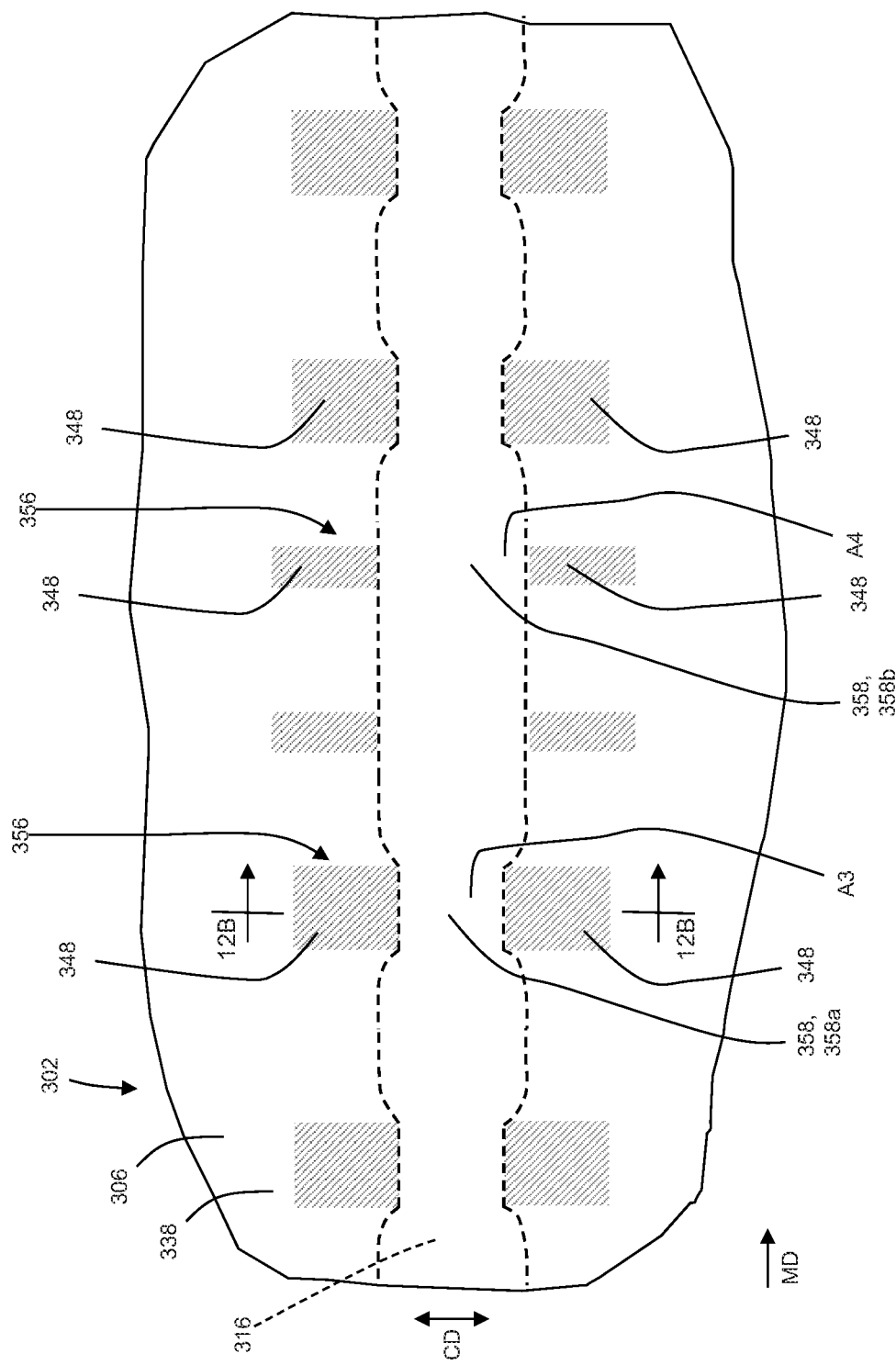
FIG. 11B is a detailed view of an elastic strand in a relaxed state bonded between the first and second substrates.

Turning next to FIGS. 11B and 12B, a detailed view of an elastic strand 316, such as shown in FIGS. 11A and 12A, is provided wherein tension has been released (or reduced) on the elastic strand 316 and showing how the tendency of the elastic strand 316 to expand creates a frictional lock in the bonded region 356. As shown in FIG. 12B, the first sleeve 358a helps prevent the cross sectional area of the elastic strand 316 from expanding beyond the third cross sectional area A3 of the first sleeve 358a when tension has on elastic strand 316 has been reduced. The tendency of the elastic strand 316 to expand creates forces F (represented by dashed double arrow lines in FIG. 12B) exerted between elastic strand 316 and the inner perimeter of the first sleeve 358a. In turn, the forces F between the elastic strand 316 and the first sleeve 358a creates a frictional lock by increasing the friction forces between the elastic strand 316 and the bonds 348 and portions of the first substrate 306 and the second substrate 308 that define the inner perimeter of the first sleeve 358a. The increased friction forces in the machine direction MD along the length of the elastic strand 316 in the first sleeve 358a holds or secures the discrete length of the elastic strand 316 in a fixed position in the first sleeve 358a together with the first and second substrates 306, 308.

In some configurations, no adhesive may be applied to and/or present between the elastic strand 316 and the first sleeves 358a. It is also to be appreciated that in some configurations, adhesive may be applied to and/or present between the elastic strand 316 and the first sleeves 358a to help the frictional lock hold the discrete length of the elastic strand 316 in a fixed position with the first and second substrates 306, 308. In some configurations, adhesive and the frictional lock in the first sleeves 358a may share the load exerted by elastic strand 316. In some configurations, adhesive positioned on the elastic strand 316 may increase the coefficient of friction between the elastic strand 316 and the first sleeve 358a. It is to be appreciated that various quantities of adhesive may be present in the first sleeve 358a, such as for example, about 10 gsm or less.

As discussed above, second channels 422b in the pattern roll 402 may be configured to create second sleeves 358b configured to create second sleeves 358b that are sized to allow the elastic strands 316 to move relative to the first and second substrates 306, 308 as the elastic strands 316 stretch and contract along machine direction MD. The second sleeve 358b may also help hold or guide the elastic strands 316 in desired positions along the cross direction CD as the elastic strands 316 stretch and contract along machine direction MD. For example, the elastic strand 316 shown in FIG. 11A may define a second cross sectional area A2 in a stretched state. The elastic strand 316 may also define a first cross sectional area A1 in a relaxed state, wherein A2 is less than A1. In turn, the second sleeves 358b may define a fourth cross sectional area A4 that may be greater than the third cross sectional area A3 of the first sleeves 358a. In some configurations, A4 may be greater than A1. As such, when the elastic strand 316 contracts and expands, no frictional bond is formed between the elastic strand and the second sleeves 358b. Thus, the elastic strand 316 is allowed to move relative to the first and second substrates 306, 308 along the machine direction MD while also being held in a fixed cross directional position.

Figure 12C:
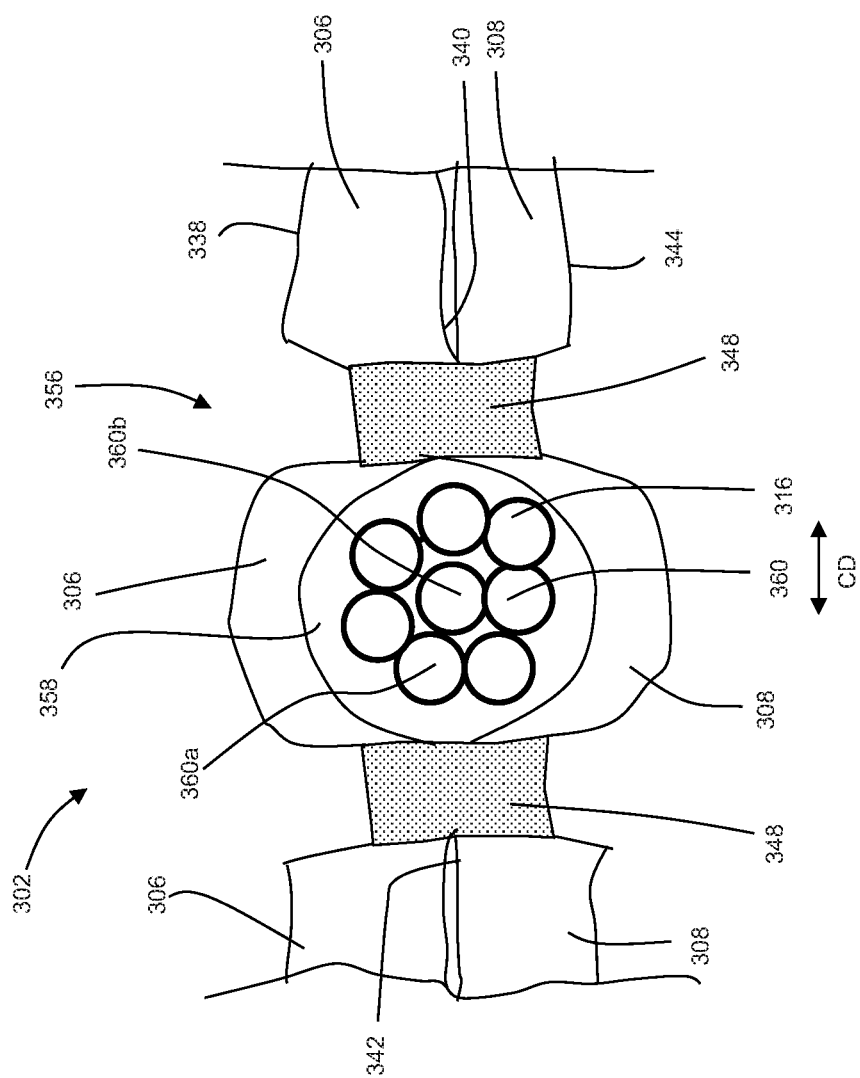
FIG. 12C is a sectional view of an elastic strand, bond, first substrate, and second substrate, wherein a plurality of filaments of the elastic strand are bonded in a first configuration.
Figure 12D:
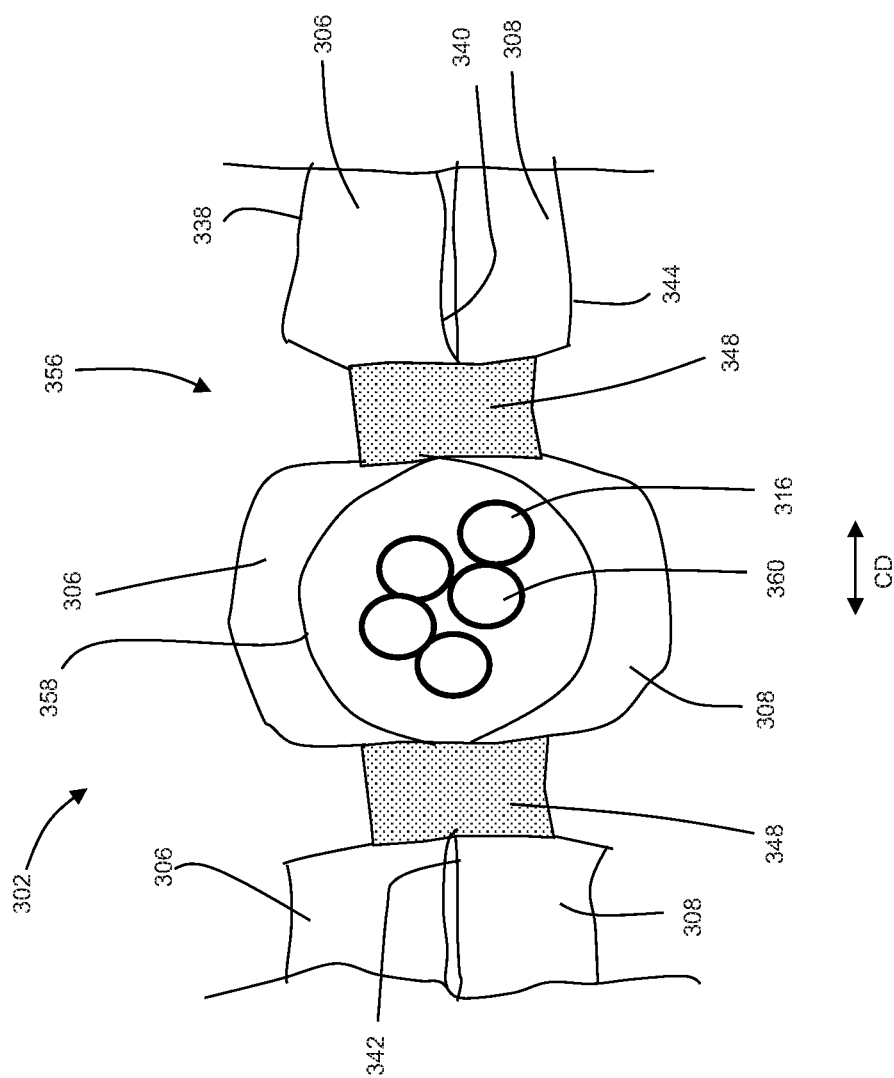
FIG. 12D is a sectional view of an elastic strand, bond, first substrate, and second substrate, wherein a plurality of filaments of the elastic strand are bonded in a second configuration.

It is also to be appreciated that the elastic strands 316 herein bonded in accordance with the methods described herein may also be constructed from one or more filaments 360. For example, FIG. 12C shows a cross sectional view of a stretched elastic strand 316 in a sleeve 358 wherein the elastic strand 316 comprises a plurality of individual filaments 360. As shown in FIG. 12C, the elastic strand 316 may include outer filaments 360a surrounding an inner filament 360b. The outer filaments 360a may define an outer perimeter of the elastic strand 316, and the outer filaments 360a may surround the inner filament 360b such that the inner filament 360b is not in contact with the sleeve 358 when the elastic strand 316 is in a relaxed state. It is to be appreciated that the filaments 360 may be arranged in various positions within the sleeve 358. For example, FIG. 12D shows a cross sectional view of an elastic strand 316 in a sleeve 358 wherein the plurality of individual filaments 360 together define a perimeter that is elongated along the cross direction CD.

As previously mentioned with reference to FIG. 5, the pattern roll 402 includes a protuberance 416 that operates to intermittently sever one or more elastic strands 316 to create deactivated regions 350 in the elastomeric laminate 302. As shown in FIGS. 8 and 9A-9C, the protuberance 416 may extend axially along the axis of rotation 406 and may extend radially outward from the axis of rotation 406 to a second radial distance R2. In some configurations, R1 may be equal to or substantially equal to R1. And in some configurations, R2>(R1−D1) and/or R2>(R1−D2). It is to be appreciated that the pattern roll 402 may include one or more protuberances 416 that may be configured in various ways with various different sizes and/or shapes. In some examples, the protuberance 416 may be configured as a discrete member that is separate from the bonding elements 412 and/or bonding surfaces 410. In some examples, the protuberance may comprise a portion of a bonding element 412 and/or bonding surface 410. In some examples, the protuberance may extend axially along the axis of rotation 406 for a distance that is equal to or less than the axial length of the pattern roll 402. The protuberance may also be positioned circumferentially between two discrete first channels 358a and/or two discrete second channels 358b.

As discussed above with reference to FIGS. 5 and 6, advancing elastic strands 316 may be joined with the first substrate 306 and the second substrate 308 to form the elastomeric laminate 302. In turn, the bond applicator 400, comprising the pattern roll 402 and the pressing surface 404, applies bonds 348 that secure the elastic strands 316 between the first substrate 306 and the second substrate 308. In addition, the bond applicator 400 severs one or more stretched elastic strands 316 to create deactivated regions 350 in the elastomeric laminate 302.

Figure 13E:
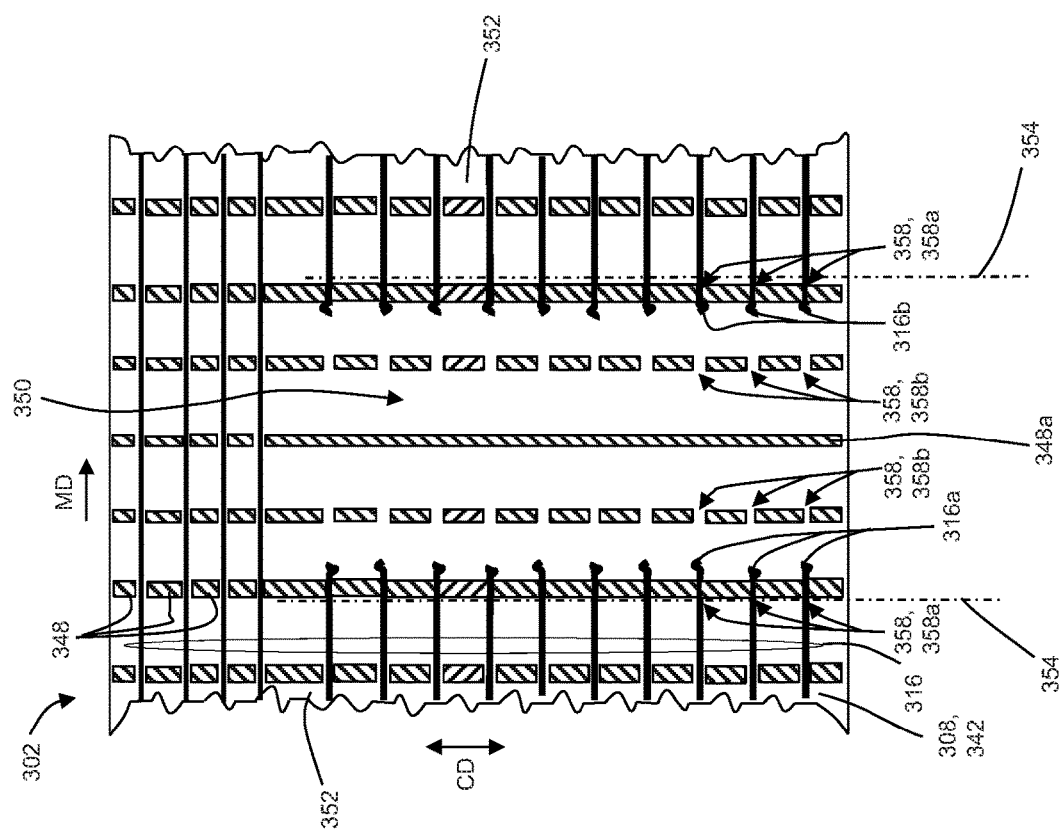
FIG. 13E shows a detailed view of an elastomeric laminate from FIG. 13D continuing to advance from the nip between the pattern roll and pressing surface to illustrate severed elastic strands having retracted to bond regions to define a deactivated region of the elastomeric laminate.

FIGS. 13A-13E provide detailed example illustrations of the elastomeric laminate 302 advancing from the nip 408 between the rotating pattern roll 402 and the pressing surface 404. For the purposes of clarity, the first substrate 306 is not shown in the views of elastomeric laminate 302 in FIGS. 13A-13E. With reference to FIGS. 5 and 13A, the first and second substrates 306, 308 with the stretched elastic strands 316 therebetween form an elastomeric laminate 302 advancing in a machine direction MD. The elastomeric laminate 302 is partially wrapped around the pattern roll 402, wherein the stretched elastic strands 316 extend through discrete channels 422 in the pattern surfaces 410, such as discussed above with reference to FIGS. 6A, 7, and 8. As the pattern roll 402 rotates, the first substrate 306 and the second substrate 308 are welded together between the bonding surfaces 410 and the pressing surface 404 to create bonds 348 between the first and second substrates 306, 308. The bonds 348 are separated from each other in the cross direction CD by the stretched elastic strands 316 positioned in respective discrete channels 422 to form sleeves 358 surrounding the stretched elastic strands 316. As discussed above with reference to FIGS. 8-11B, the pattern roll 402 may include first channels 422a configured to create first sleeves 358a that are sized to secure discrete lengths of the elastic strands 316 in fixed positions relative to the first and second substrates 306, 308 with a frictional lock. And the second channels 422b may be configured to create second sleeves 358b that are sized to allow the elastic strands 316 to move relative to the first and second substrates 306, 308 as the elastic strands 316 stretch and contract along machine direction MD while at the same time holding and/or guiding the elastic strands 316 in desired positions along the cross direction CD. FIG. 13A illustrates an example arrangement of first and second sleeves 358a, 358b along the machine direction MD of the elastomeric laminate 302.

As discussed above with reference to FIGS. 8 and 9C, the pattern roll 402 also includes one or more protuberances 416 that sever one or more stretched elastic strands 316 to create deactivated regions 350 in the elastomeric laminate 302. With reference to FIG. 13B, as the pattern roll 402 continues to rotate, the first substrate 306, the second substrate 308, and one or more stretched elastic strands 316 are compressed between the pressing surface 404 and the protuberance 416 to sever the one or more stretched elastic strands 316. As shown in FIG. 13B, the protuberance 416 may also comprise a bonding surface 410 that also welds the first and second substrates 306, 308 together with a bond 348a while also operating to sever the elastic strands 316.

As shown in FIG. 13B, upstream ends 316a and downstream ends 316b of the severed elastic strands 316 may begin to retract in opposing directions. As previously mentioned, the first substrate 306, the second substrate 308, and the stretched elastic strands 316 may be partially wrapped onto the rotating pattern roll 402. And tension exerted on the first and second substrates 306, 308 and the stretched elastic strands 316 forces the elastomeric laminate 302 against a portion of the pattern roll 402 upon which the elastomeric laminate 302 is wrapped. As such, the tension and resulting forces causes the first and second substrates 306, 308 to press against each other and against the stretched elastic strands 316 therebetween. Thus, as the stretched elastic strands 316 are severed, pressure exerted by the substrates 306, 308 on the elastic strands 316 therebetween may help the ends 316a, 316b of the severed elastic strands 316 retract or snap back at a relatively slower and/or controlled rate.

As shown in FIGS. 13C and 13D, as the pattern roll 402 continues to rotate, additional bonds 348 may be applied to the elastomeric laminate 302 upstream of retracting upstream ends 316a of the severed elastic strands 316. As shown in FIG. 13E, the ends 316a, 316b of the elastic strands 316 may retract to first sleeves 358a until a frictional lock is created between the elastic strands 316 and the first sleeves 358a. In turn, the frictional lock prevents the ends 316a, 316b of the elastic strands 316 from further retraction relative to the first and second substrates 306, 308. Retraction of the severed elastic strands 316 creates a deactivated region 350 in the elastomeric laminate 302. For the purposes of clarity, dashed lines 354 are shown in FIG. 13E to represent example boundaries between the deactivated regions 350 and the elastomeric regions 352 of the elastomeric laminate 302. Also, as shown in FIGS. 13C and 13D, the ends 316a, 316b of the severed elastic strands 316 retract through the second sleeves 316b while at the same time being guided along the machine direction MD by the second sleeves 358b while retracting.

It is to be appreciated that different components may be used to construct the elastomeric laminates 302 in accordance with the methods and apparatuses herein. For example, the first and/or second substrates 306, 308 may include nonwovens and/or films and may be constructed from various types of materials, such as plastic films; apertured plastic films; woven or nonwoven webs of natural materials, such as wood or cotton fibers; synthetic fibers, such as polyolefins, polyamides, polyester, polyethylene, or polypropylene fibers or a combination of natural and/or synthetic fibers; or coated woven or nonwoven webs; polymeric films such as thermoplastic films of polyethylene or polypropylene, and/or a multi-layer or composite materials comprising a film and a nonwoven material.

It is also to be appreciated that the strands 316 and/or filaments 360 herein may define various different cross-sectional shapes. For example, in some configurations, strands 316 or filaments 360 may define circular, oval, or elliptical cross sectional shapes or irregular shapes, such as dog bone and hourglass shapes. In addition, the elastic strands 316 may be configured in various ways and with various decitex values. In some configurations, the elastic strands 316 may be configured with decitex values ranging from about 10 decitex to about 500 decitex, specifically reciting all 1 decitex increments within the above-recited range and all ranges formed therein or thereby.

Figure 5A:
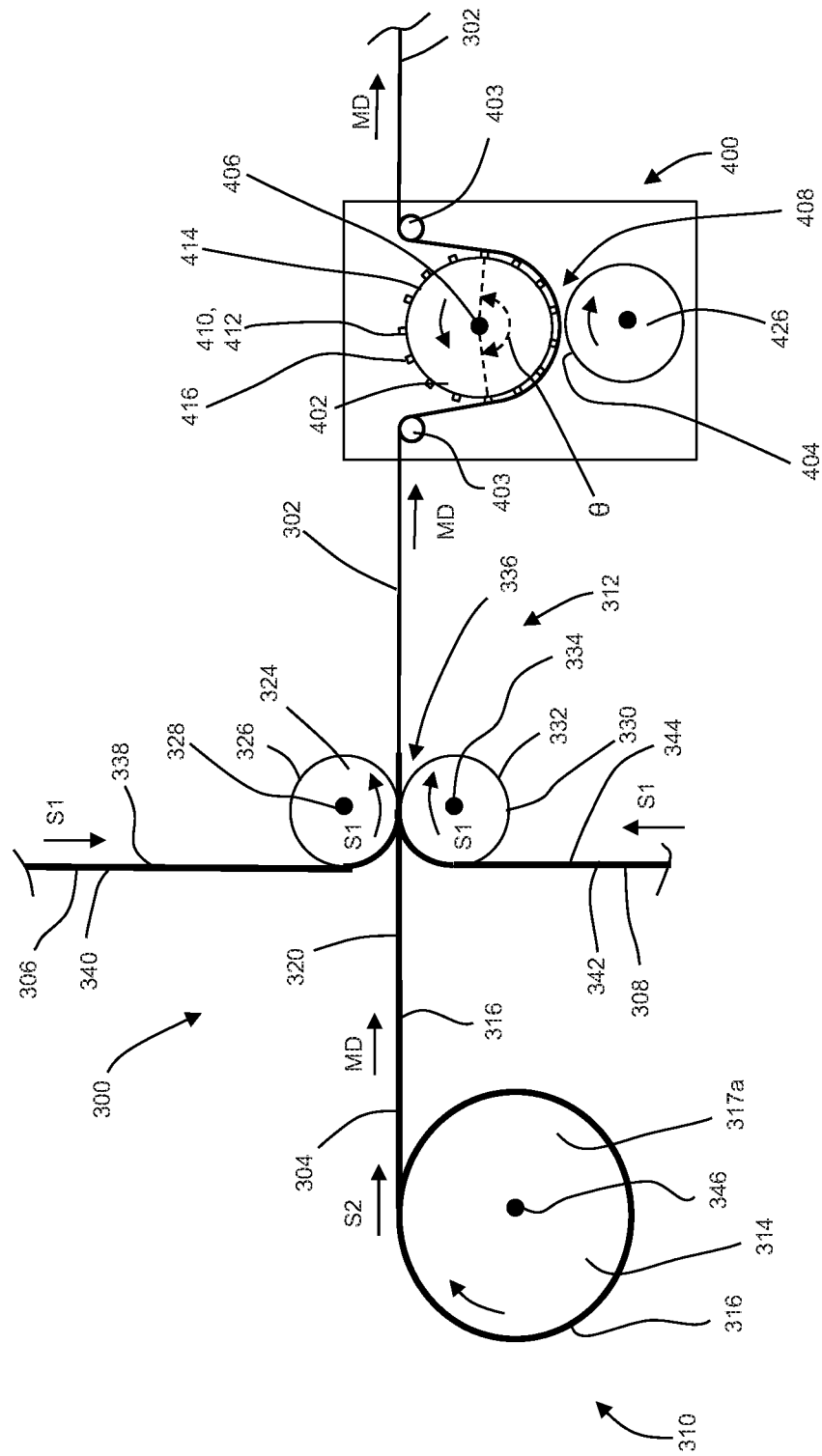
FIG. 5A is a schematic side view of a converting apparatus with a bonding apparatus configured with an anvil.

It is to be appreciated that the bond applicator 400 herein may be configured in various ways with various features described herein to assemble elastomeric laminates 302. For example, as shown in FIG. 5A, the bond applicator 400 may be configured as a mechanical bonding device that includes an anvil 426 that defines the pressing surface 404 operating in conjunction with the pattern roll 402. As such, the pattern roll 402 and/or anvil 426 may be configured to apply heat and pressure in various other ways to perform the bonding and cutting operations described above, such as for example, the mechanical bonding devices and methods disclosed in U.S. Pat. Nos. 4,854,984; 6,248,195; 8,778,127; and 9,005,392; and U.S. Patent Publication Nos. 2014/0377513 A1; and 2014/0377506 A1.

Figure 5B:
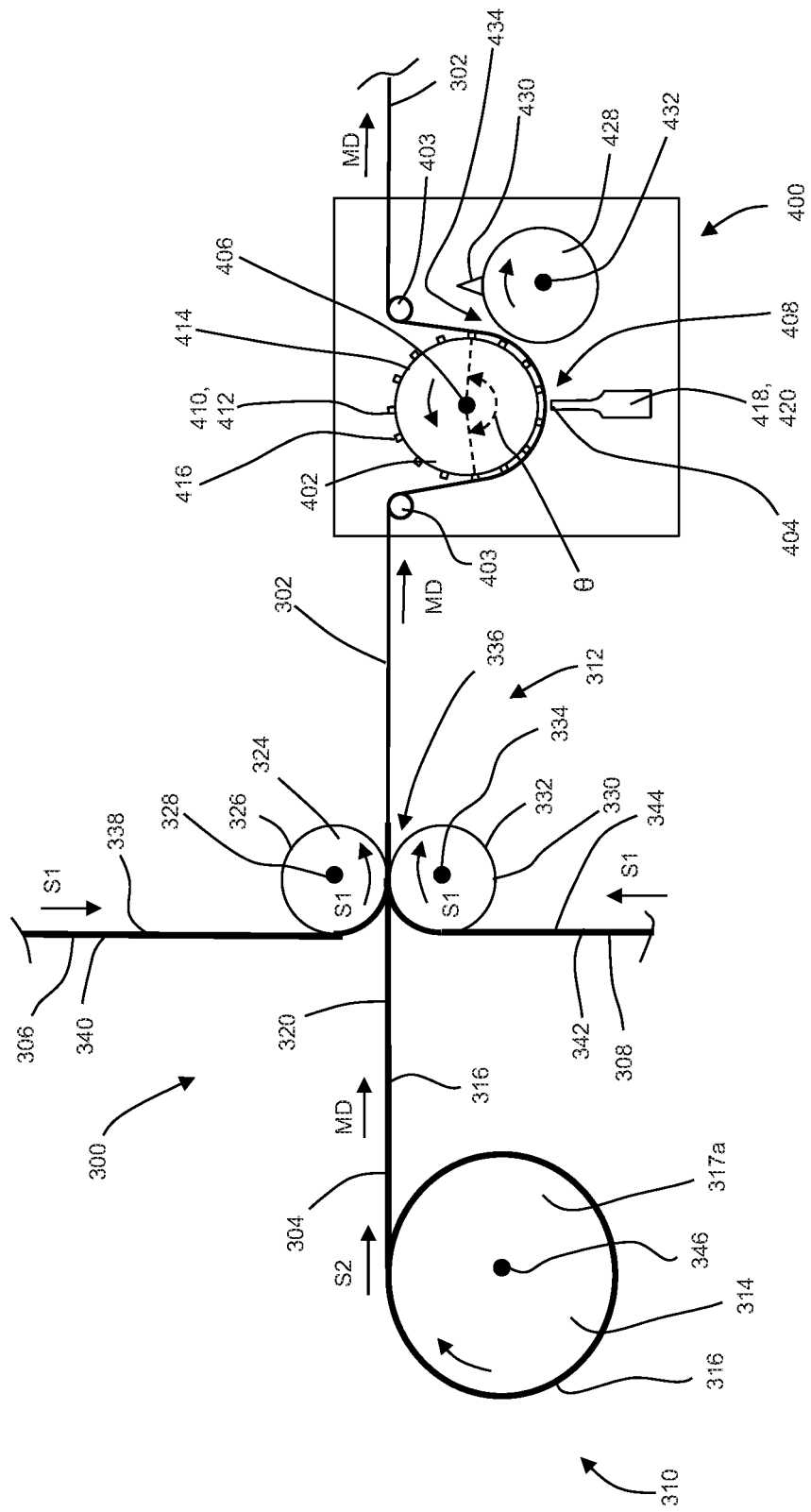
FIG. 5B is a schematic side view of a converting apparatus with a bonding apparatus configured with a cutting roll adapted to engage the pattern roll.

As discussed above, the pattern roll 402 includes a protuberance 416 that engages the pressing surface 404 to intermittently sever one or more elastic strands 316 to create deactivated regions 350 in the elastomeric laminate 302. In some configurations, the one or more elastic strands 316 may be severed downstream of the pressing surface 404. For example, as shown in FIG. 5B, the bond applicator 400 may be configured to include a cutting roll 428 that may include one or more blades 430 and adapted to rotate around an axis of rotation 432. The cutting roll 428 may also be positioned adjacent the pattern roll 402 to define a nip 434 therebetween positioned downstream of the nip 408 between the pattern roll 402 and the pressing surface 404. In operation, the elastomeric laminate 302 advances through the nip 408 between the pattern roll 402 and the pressing surface 404 to apply the bonds 348 that secure the elastic strands 316 between the first substrate 306 and the second substrate 308. However, the protuberance 416 on the pattern roll 402 may be configured such that the elastomeric laminate 302 advances between the protuberance 416 and the pressing surface 404 without severing elastic strands 316. For example, as discussed above with reference to FIGS. 8 and 9C, the protuberance 416 may extend axially along the axis of rotation 406 and may extend radially outward from the axis of rotation 406 to a second radial distance R2. As such, the second radial distance R2 may be relatively small such that the elastic strands 316 are not severed between the protuberance 416 and the pressing surface 404. In turn, the elastomeric laminate 302 advances from the nip 408 to the nip 434 between the cutting roll 428 and the pattern roll 402 wherein the blade 430 engages the protuberance 416 to sever one or more elastic strands 316 to create deactivated regions 350 in the elastomeric laminate 302.

It is to be appreciated that various configurations of cutting rolls 428 can be used with the apparatuses and methods herein. Such cutting roll configurations may include features of the cutting blades/units disclosed, for example, in U.S. Pat. Nos. 5,393,360; 7,708,849; 7,861,756; 7,777,094; and 8,440,043; and U.S. Patent Publication No. 2013/0261589 A1, which are all incorporated by reference herein. As such, the cutting rolls may be configured with die knife, flexible blade, and/or compression roll features, and may also include additional features to control knife-anvil gaps and/or force.

As discussed above, the pattern roll 402 may include one or more protuberances 416 that may be configured in various ways with various different sizes and/or shapes. For example as shown in FIG. 8A, the protuberance 416 may be configured as one or more discrete members 436 that are separate from the bonding elements 412 and/or bonding surfaces 410. The discrete members 436 may also be axially offset with respect to the channels 422, and as such, may also be configured to the bond the first and second substrates 306, 308 together while simultaneously severing the elastic strands 316. As shown in FIG. 14A, the discrete members 436 may create discrete bonds 348a shaped and arranged in a pattern corresponding with the shapes of the discrete members 436. In another configuration shown in FIG. 14B, the protuberance 416 and/or the discrete members 436 may be configured to cut the elastic strands 316 into one or more discrete lengths or pieces 316c in the deactivated region 350.

It is to be appreciated that the apparatuses 300 herein may be configured in various ways with various features described herein to assemble elastomeric laminates 302 having various stretch characteristics. For example, the apparatus 300 may be configured to assemble elastomeric laminates 302 with elastic strands 316 unwound from more than one beam 314 and/or in combination with elastic stands supplied from an overend unwinder. The elastic strands 316 may be joined with the first and second substrates 306, 308 such that the elastomeric laminate 302 may have different stretch characteristics in different regions along the cross direction CD. For example, when the elastomeric laminate 302 is elongated, the first elastic strands 316 may exert contraction forces in the machine direction MD that are different from contraction forces exerted by the second elastic strands 316. Such differential stretch characteristics can be achieved by stretching the first elastic strands 316 more or less than the second elastic strands 316 before joining the elastic strands with the first and second substrates 306, 308. It is also appreciated that the elastic strands 316 may have various different material constructions and/or decitex values to create elastomeric laminates 302 having different stretch characteristics in different regions. In some configurations, the elastomeric laminate may have regions where the elastic strands 316 are spaced relatively close to one another in the cross direction CD and other regions where the elastic strands 316 are spaced relatively farther apart from each other in the cross direction CD to create different stretch characteristics in different regions. In some configurations, the elastic strands 316 may be supplied on the beam 314 in a stretched state, and as such, may not require additional stretching (or may require relatively less additional stretching) before being combined with the first substrate 306 and/or the second substrate 308.

As previously mentioned, the first substrate and second substrate 306, 308 herein may be defined by two discrete substrates or may be defined by folded portions of a single substrate. In addition, the second metering device 312 may also be configured as the bond applicator 400. For example, as shown in FIG. 15, the first substrate 306 may advance at speed S1 to the first roller 324 where the first substrate 306 partially wraps around the pattern roll 402. While partially wrapped around the pattern roll 402, the first substrate 306 is combined with the elastic strands 316. As the beam 314 rotates, the elastic strands 316 advance from the beam 314 at a speed S2 with the elastic strands 316 being spaced apart from each other in the cross direction CD. From the beam 314, elastic strands 316 advance to the pattern roll 402 and are positioned on the second surface 340 of the first substrate 306. As shown in FIGS. 15 and 16, a folding device 438 may operate to fold a first portion 306a onto a second portion 306b of the first substrate 306 with the elastic strands 316 positioned between the first and second portions 306a, 306b to create the elastomeric laminate 302. As shown in FIGS. 15 and 17, the pressing surface 404 may be configured to apply the bonds 348 and intermittently sever one or more elastic strands 316 before elastomeric laminate 302 advances from the pattern roll 402.

It is to be appreciated that the elastomeric laminates 302 may be used to construct various types of absorbent article components. For example, the elastomeric laminates 302 may be used as a continuous length of elastomeric belt material that may be converted into the first and second elastic belts 106, 108 discussed above with reference to FIGS. 1-3B. As such, the elastic material 304 may correspond with the belt elastic material 168 interposed between the outer layer 162 and the inner layer 164, which in turn, may correspond with either the first and/or second substrates 306, 308. In other examples, the elastomeric laminates may be used to construct waistbands and/or side panels in taped diaper configurations. In yet other examples, the elastomeric laminates may be used to construct various types of leg cuff and/or topsheet configurations.

This application claims the benefit of U.S. Provisional Application Nos. 62/436,589, filed on Dec. 20, 2016; 62/483,965, filed on Apr. 11, 2017; 62/553,538, filed on Sep. 1, 2017; 62/553,149, filed on Sep. 1, 2017; 62/553,171, filed on Sep. 1, 2017; and 62/581,278, filed on Nov. 3, 2017, the entireties of which are all incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an elastomeric laminate, the method comprising steps of:
   rotating a pattern roll about an axis of rotation extending axially in a cross direction, the pattern roll comprising: first bonding elements extending outward from an outer circumferential surface of the pattern roll each comprising a bonding surface; discrete first channels in each bonding surface of a depth not entirely through the first bonding elements, wherein the discrete first channels are circumferentially spaced apart from each other and spaced apart from each other axially in the cross direction, and a protuberance extending axially in the cross direction between two of the discrete first channels;
   providing a pressing surface adjacent the pattern roll;
   providing an elastic strand, wherein the elastic strand defines a first cross sectional area in an unstretched state;
   stretching the elastic strand, wherein the stretched elastic strand defines a second cross sectional area that is less than the first cross sectional area;

advancing a first substrate and a second substrate with the stretched elastic strand between the first substrate and the second substrate in a machine direction;

partially wrapping the first substrate, the second substrate, and the stretched elastic strand on the pattern roll to cause the first substrate and the second substrate to press against each other and against the stretched elastic strand, wherein the stretched elastic strand extends through at least one discrete first channel;

welding the first substrate and the second substrate together between a bonding surface and the pressing surface to create bonds between the first substrate and the second substrate, wherein the bonds are separated from each other in the cross direction by the stretched elastic strand positioned in the at least one discrete first channel to form a first sleeve surrounding the stretched elastic strand, wherein the first sleeve defines a third cross sectional area that is less than the first cross sectional area and equal to or greater than the second cross sectional area;

compressing the first substrate, the second substrate, and the elastic strand between the pressing surface and the protuberance to sever the stretched elastic strand while the first substrate, the second substrate, and the elastic strand are partially wrapped on the pattern roll, wherein the severed elastic strand retracts and expands to create a frictional lock between the first sleeve and the severed elastic strand.

2. The method of claim 1, wherein the pressing surface comprises an energy transfer surface of an ultrasonic horn.

3. The method of claim 1, wherein the pattern roll further comprises a second discrete channel in a second bonding element having a bonding surface, and further comprising the step of: welding the first substrate and the second substrate together between the bonding surface and the pressing surface to form bonds between the first substrate and the second substrate, wherein the bonds are separated from each other in the cross direction by the stretched elastic strand positioned in the second channel to form a second sleeve surrounding the stretched elastic strand, wherein the second sleeve defines a fourth cross sectional area that is greater than the third cross sectional area.

4. The method of claim 3, wherein the second sleeve guides the severed elastic strand along the machine direction as the severed elastic strand retracts.

5. The method of claim 1, further comprising a step of welding the first substrate together with the second substrate by compressing the first substrate and the second substrate between the pressing surface and the protuberance.

6. The method of claim 1, wherein the protuberance comprises a bonding surface.

7. The method of claim 1, wherein the elastic strand comprises a spin finish.

8. The method of claim 1, wherein the elastic strand comprises a plurality of filaments.

9. The method of claim 1, wherein each bonding surface is defined by the first bonding elements extending radially outward from the outer circumferential surface of the pattern roll, wherein each bonding surface is positioned at a first radial distance R1 from the axis of rotation, and the discrete first channels extend radially into the first bonding elements from the bonding surface to a first depth D1.

10. The method of claim 9, wherein the protuberance extends radially outward from the axis of rotation to a second radial distance R2, and wherein R2>(R1−D1).

11. A method for making absorbent articles, the method comprising steps of:

rotating a pattern roll about an axis of rotation extending axially in a cross direction, the pattern roll comprising: first bonding elements extending outward from an outer circumferential surface of the pattern roll each comprising a bonding surface; discrete first channels in each bonding surface of a depth not entirely through the first bonding elements, wherein the discrete first channels are spaced apart from each other circumferentially and spaced apart from each other axially in the cross direction; and a protuberance extending axially in the cross direction between two of the discrete first channels;

providing a pressing surface adjacent the pattern roll;

providing elastic strands, wherein each elastic strand defines a first cross sectional area in an unstretched state;

stretching the elastic strands, wherein each stretched elastic strand defines a second cross sectional area that is less than the first cross sectional area;

forming an elastomeric laminate by positioning the stretched elastic strands between a first substrate and a second substrate, wherein the stretched elastic strands are separated from each other in the cross direction;

advancing the elastomeric laminate in a machine direction;

partially wrapping the elastomeric laminate on the pattern roll to cause the first substrate and the second substrate to press against each other and against the stretched elastic strands, wherein the stretched elastic strands extend through respective discrete first channels;

welding the first substrate and the second substrate together between a bonding surface and the pressing surface to form bonds between the first substrate and the second substrate, wherein the bonds are separated from each other in the cross direction by the stretched elastic strands positioned in the discrete first channels to form first sleeves surrounding the stretched elastic strands, wherein each first sleeve defines a third cross sectional area that is less than the first cross sectional area and equal to or greater than the second cross sectional area; and forming a deactivated region in the elastomeric laminate positioned along the machine direction between elasticized regions by compressing the first substrate, the second substrate, and at least one stretched elastic strand between the pressing surface and the protuberance to sever the at least one stretched elastic strand while the elastomeric laminate is partially wrapped on the pattern roll, wherein the at least one severed elastic strand retracts and expands to create a frictional lock between the first sleeve and the at least one severed elastic strand.

12. The method of claim 11, wherein the pressing surface comprises an energy transfer surface of an ultrasonic horn.

13. The method of claim 11, wherein the pattern roll further comprises a second discrete channel in a second bonding element having a bonding surface, and further comprising the step of: welding the first substrate and the second substrate together between the bonding surface and the pressing surface to form bonds between the first substrate and the second substrate, wherein the bonds are separated from each other in the cross direction by the at least one stretched elastic strand positioned in the second channel to form a second sleeve surrounding the at least one stretched elastic strand, wherein the second sleeve defines a fourth cross sectional area that is greater than the third cross sectional area.

14. The method of claim 13, wherein the second sleeve guides the at least one severed elastic strand along the machine direction as the at least one severed elastic strand retracts.

15. The method of claim 11, further comprising a step of welding the first substrate together with the second substrate by compressing the first substrate and the second substrate between the pressing surface and the protuberance.

16. The method of claim 11, wherein the protuberance comprises a bonding surface.

17. The method of claim 11, further comprising a step of bonding the first substrate and the second substrate together in the deactivated region.

18. The method of claim 11, further comprising steps of:
    providing an absorbent chassis comprising a topsheet, a backsheet, and an absorbent core disposed between the topsheet and the backsheet, the absorbent chassis further comprising a first end region and an opposing second end region separated from each other by a central region, and having a longitudinal axis and a lateral axis; and
    bonding the first end region of the absorbent chassis with the deactivated region of the elastomeric laminate.

19. The method of claim 18, further comprising a step of bonding a second elastomeric laminate with the second end region of the absorbent chassis.

20. The method of claim 19, further comprising steps of:
    folding each chassis along the lateral axis to position the elastomeric laminate into a facing relationship with the second elastomeric laminate; and
    bonding the elastomeric laminate with the second elastomeric laminate to form pant diaper side seams.

* * * * *